United States Patent [19]

Wanderer et al.

[11] Patent Number: 5,181,524
[45] Date of Patent: * Jan. 26, 1993

[54] NEEDLE GUARD FOR BLOOD COLLECTION

[75] Inventors: Alan A. Wanderer, Englewood; William E. Sagstetter, Denver, both of Colo.

[73] Assignee: Medical Safety Products, Inc., Denver, Colo.

[*] Notice: The portion of the term of this patent subsequent to Mar. 15, 2005 has been disclaimed.

[21] Appl. No.: 765,956

[22] Filed: Sep. 26, 1991

Related U.S. Application Data

[60] Division of Ser. No. 353,898, Apr. 13, 1989, abandoned, which is a continuation-in-part of Ser. No. 918,020, Oct. 14, 1986, Pat. No. 4,731,059, and a continuation-in-part of Ser. No. 919,373, Oct. 16, 1986, Pat. No. 4,693,708.

[51] Int. Cl.$^5$ .................. A61B 5/00; A61M 5/32
[52] U.S. Cl. .................. 128/764; 128/765; 604/198
[58] Field of Search .............. 604/110, 162, 163, 192, 604/197, 198, 201, 205, 241, 263, 272, 412–414; 128/763–765

[56] References Cited

U.S. PATENT DOCUMENTS 2,757,672  8/1956  Ogle .................. 604/241
4,743,233  5/1988  Schneider .................. 604/192

Primary Examiner—C. Fred Rosenbaum
Assistant Examiner—Anthony Gutowski
Attorney, Agent, or Firm—Cahill, Sutton & Thomas

[57] ABSTRACT

A needle guard attached to the barrel of a hypodermic syringe encloses and shields the needle against contamination prior to use and prevents inadvertent direct contact therewith by medical personnel after use. Development of an aperture at the end of the needle shield to accommodate protrusion by the needle is effected by a removable member. Translation of the needle guard along the syringe barrel to uncover and recover the needle is effected by manipulation from a location rearwardly of the needle point to further protect the medical personnel. A double ended needle, usually used with a collection tube holder of a blood evacuation system, includes a needle guard which may interlock with the holder upon translation of the needle guard to expose the anterior needle and to prevent inadvertent disengagement with the holder and resulting exposure of the posterior needle. An extension of the interconnection between the double ended needle and the holder permits large girth holders to be employed without compromising the preferred needle entry angle. Other embodiments of the needle guard include telescoping guards to shield lengthy single needles and double-ended needles, each of which is manipulated from a location rearwardly of the respective needle end. The configuration of the needle guard permits manipulation with only one digit of one hand which frees the other hand to perform functions related to blood collection or injection. An annular trough within the needle guard restrains outflow of and contamination by any fluids which may have dripped from the needle into the needle guard.

3 Claims, 13 Drawing Sheets

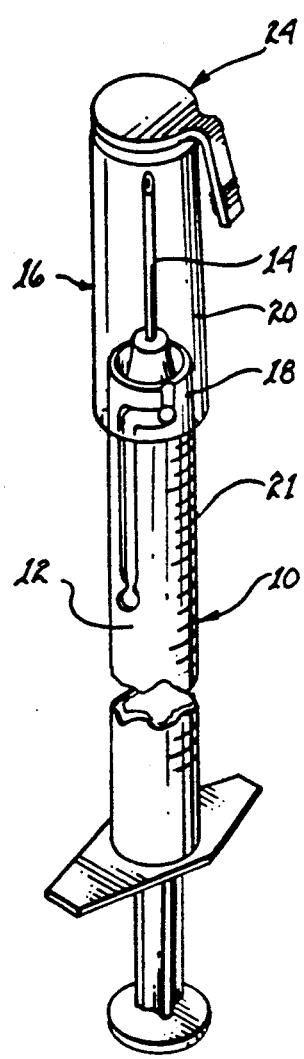
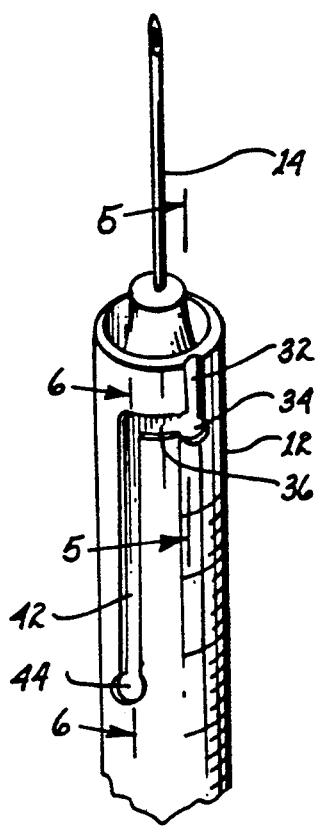
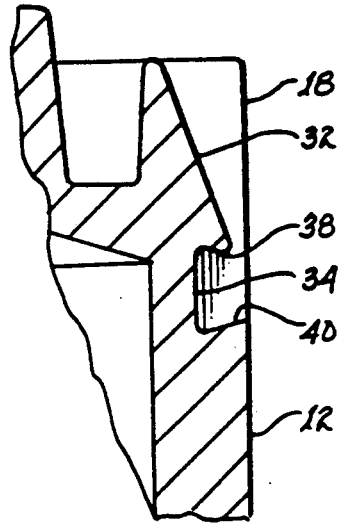
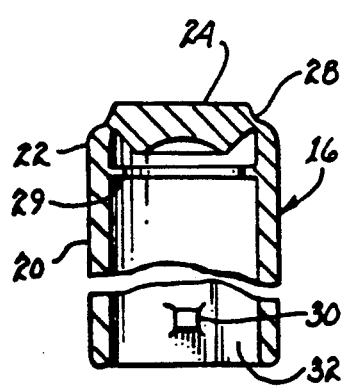
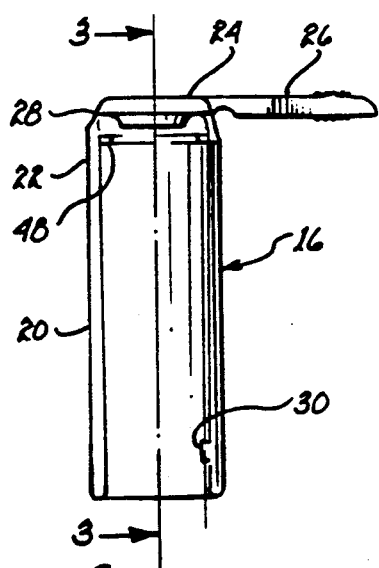
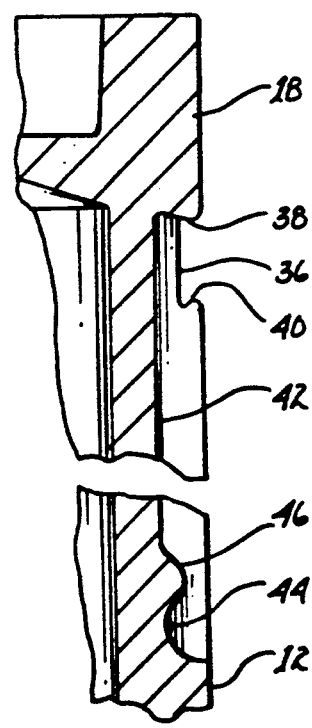
fig. 1
fig. 4
fig. 5
fig. 3
fig. 2
fig. 6

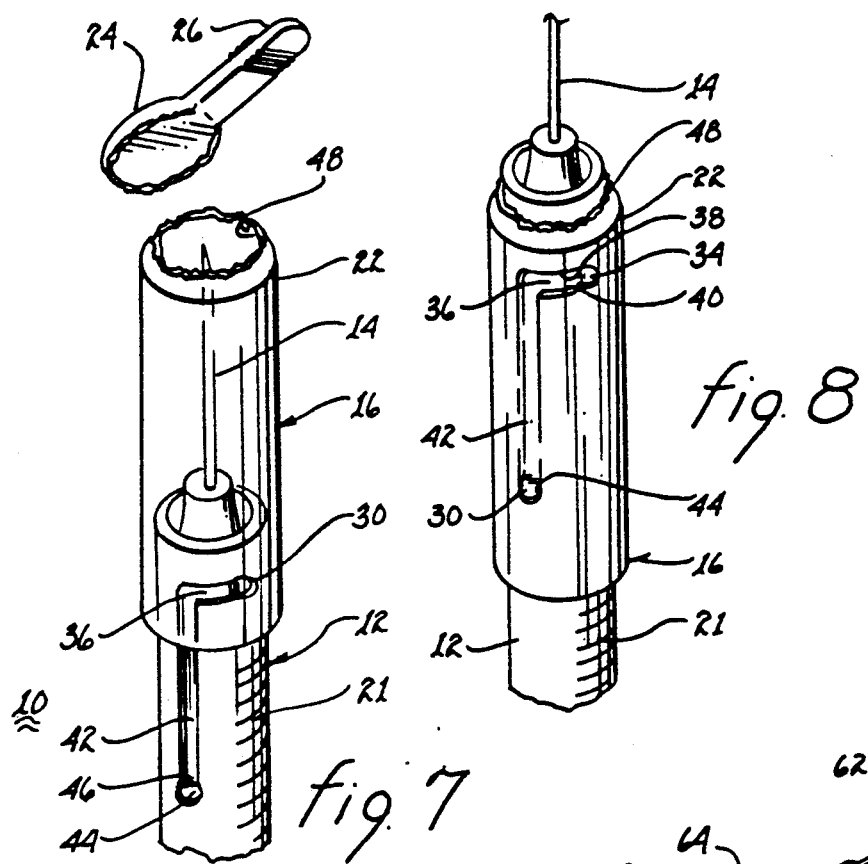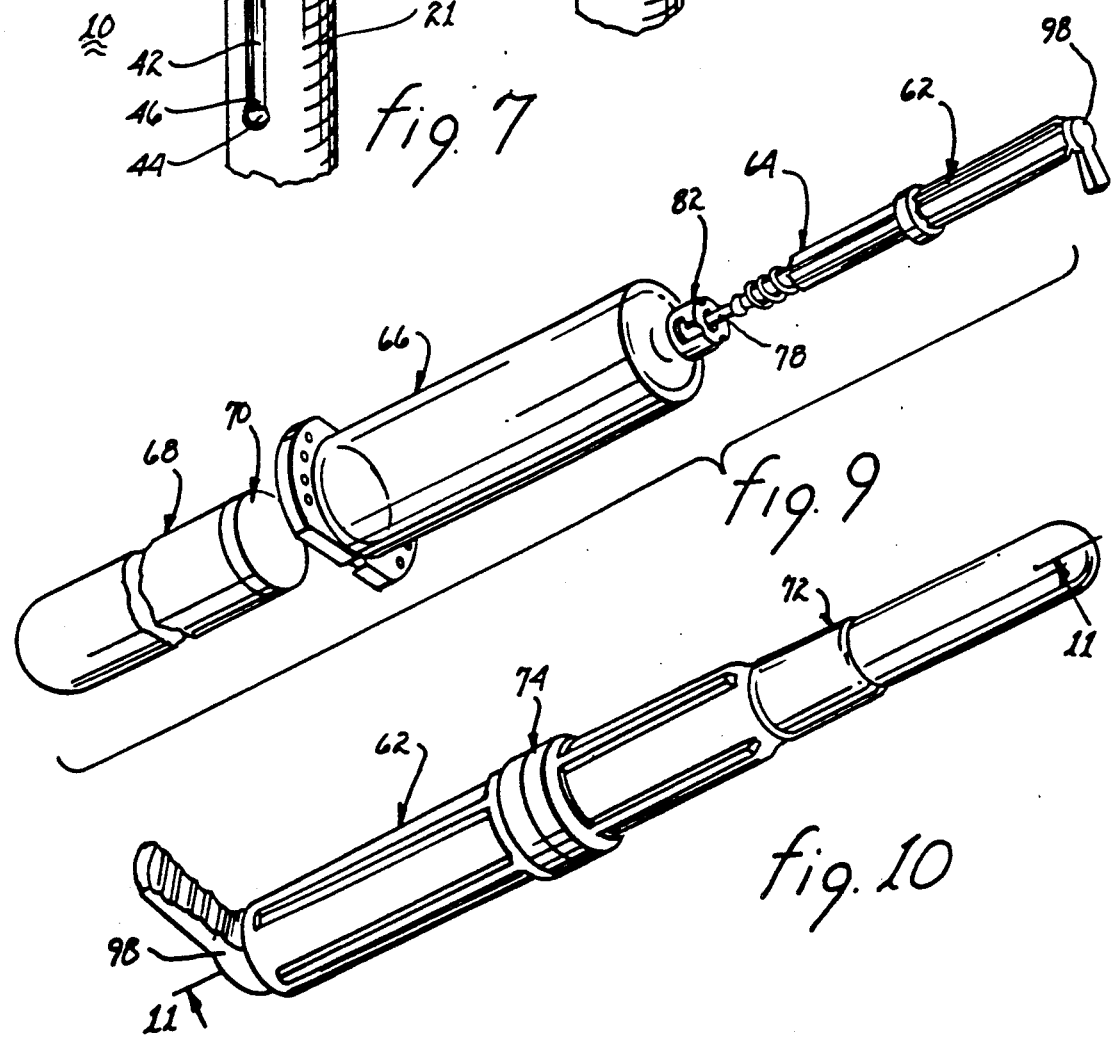

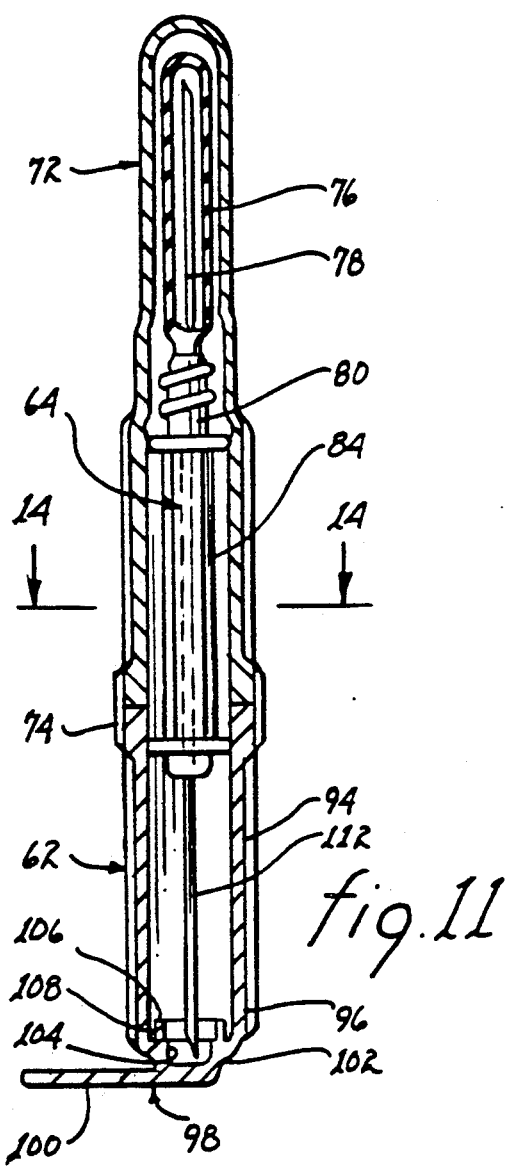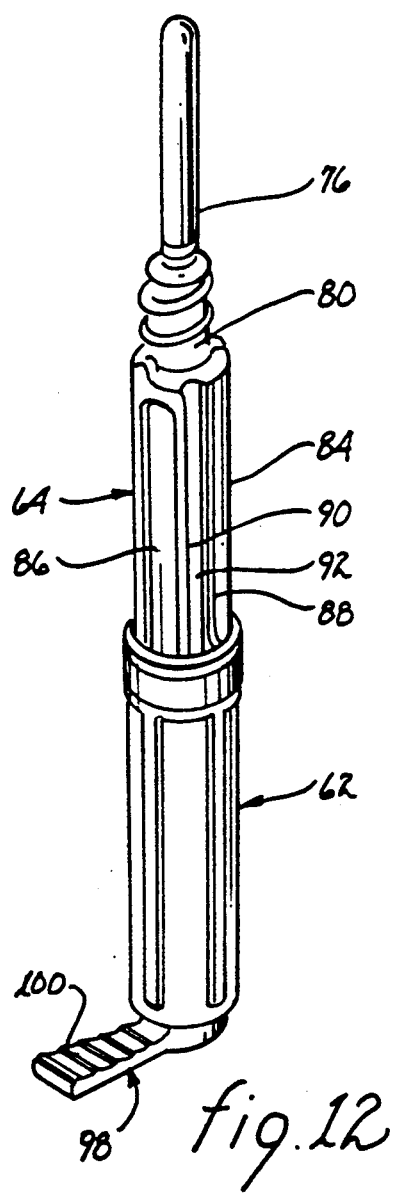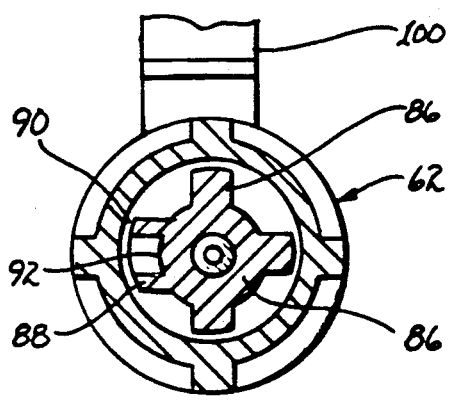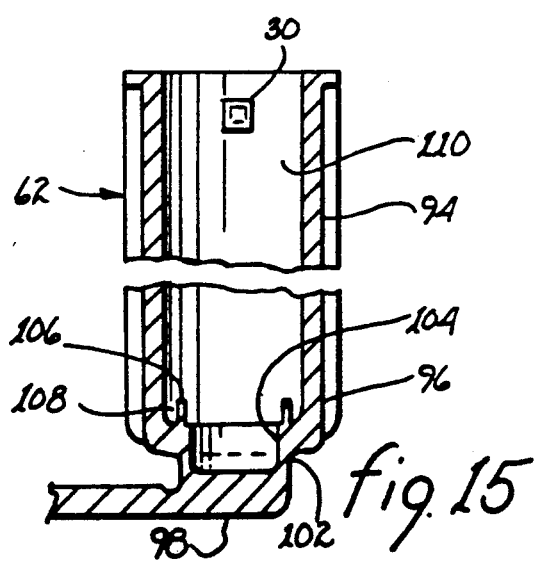

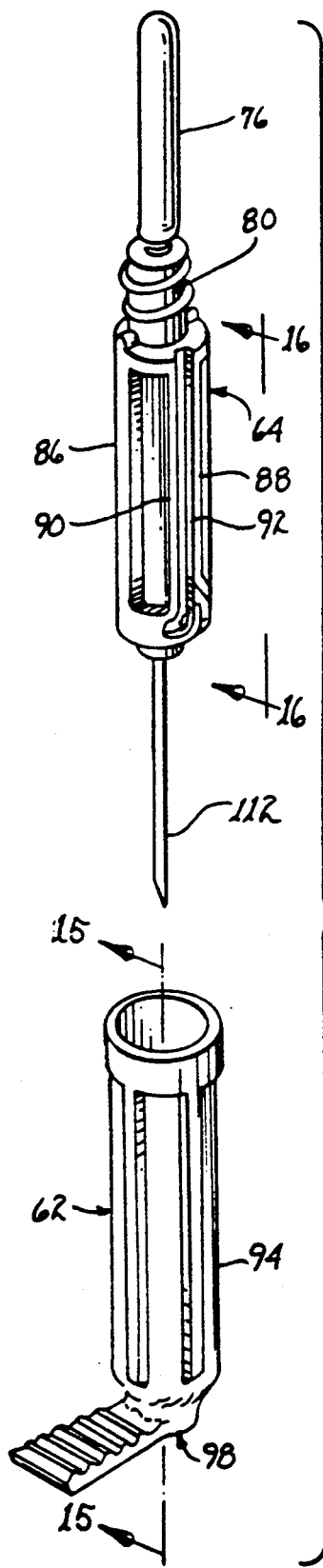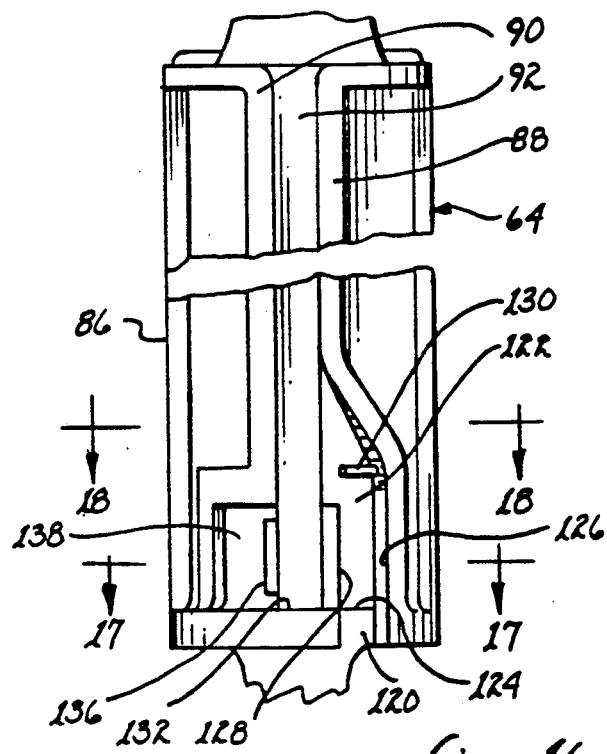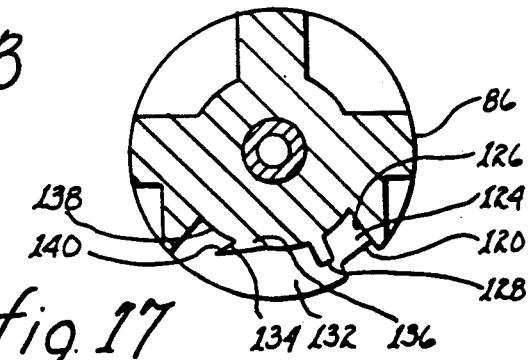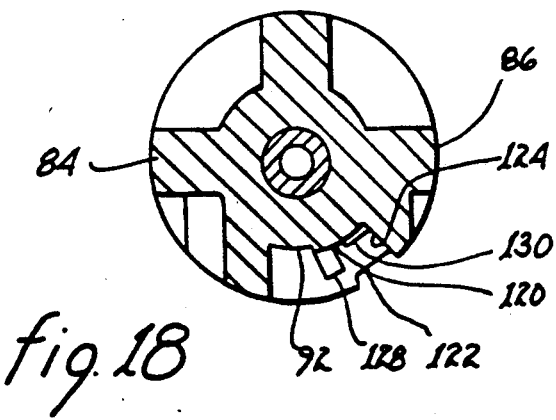

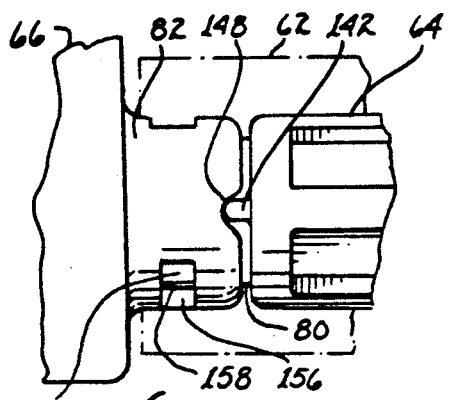
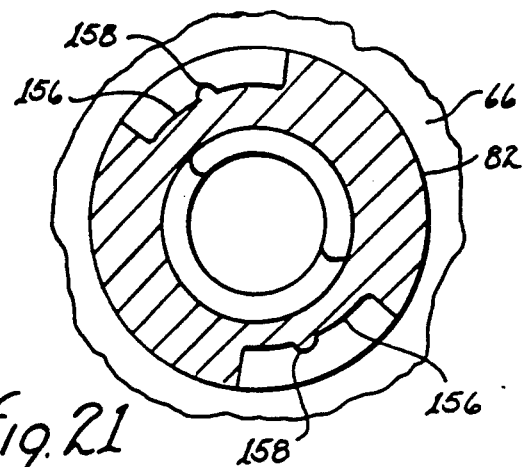
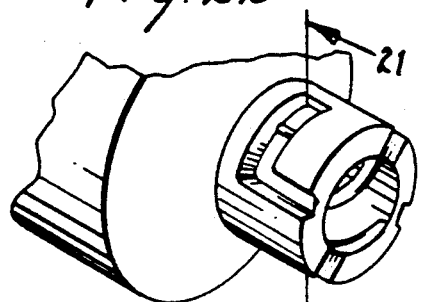
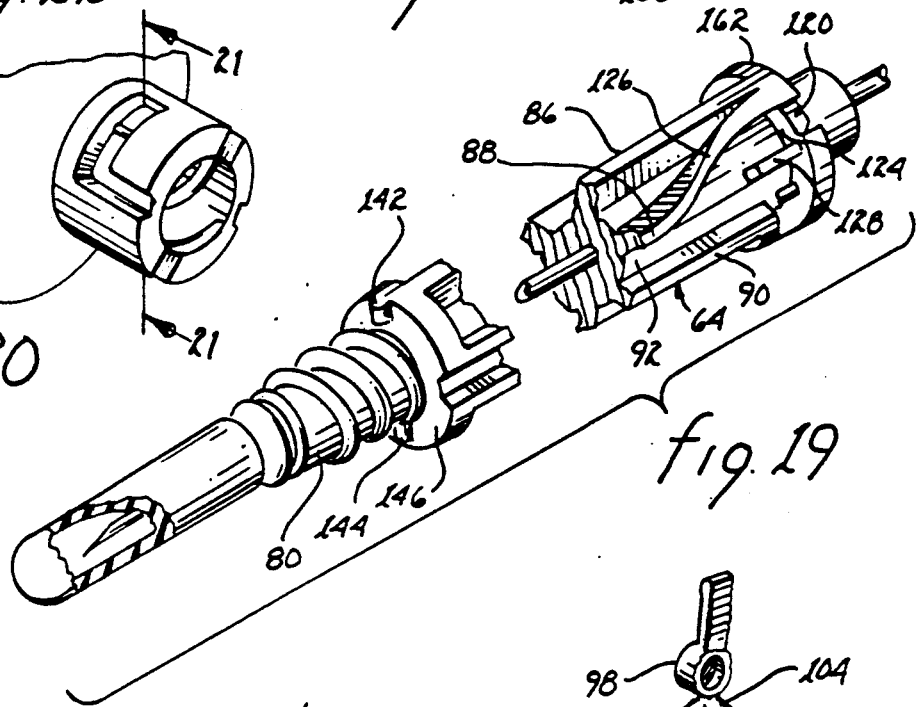
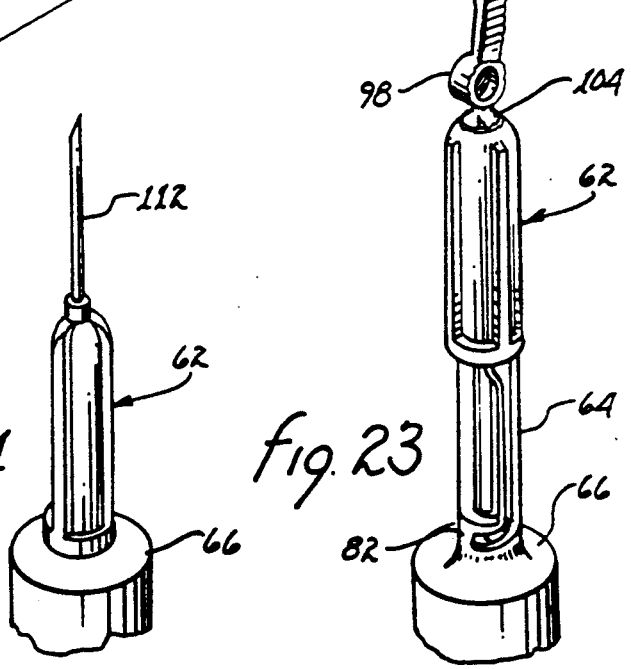
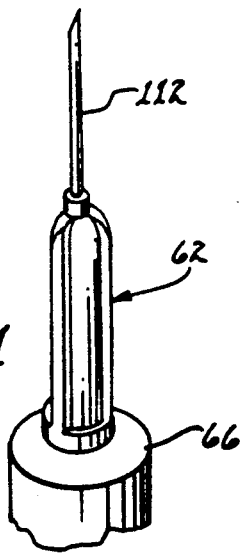

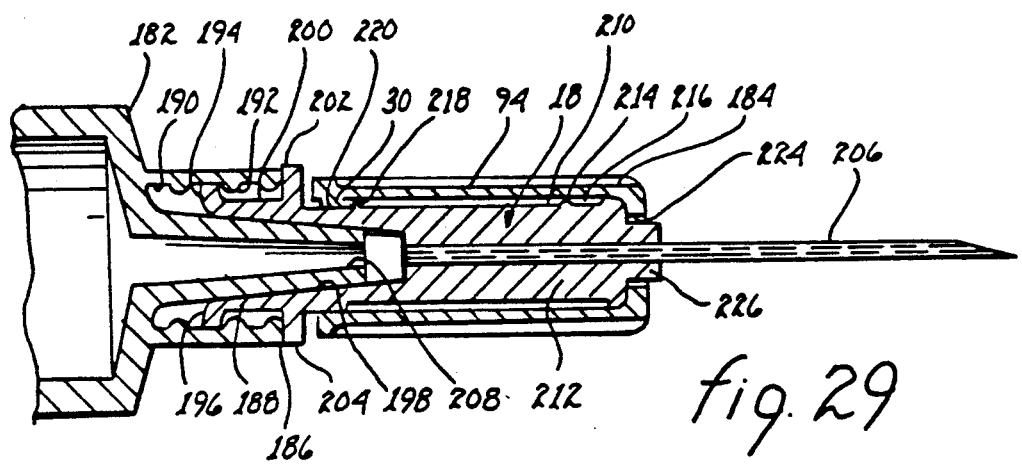
fig. 29
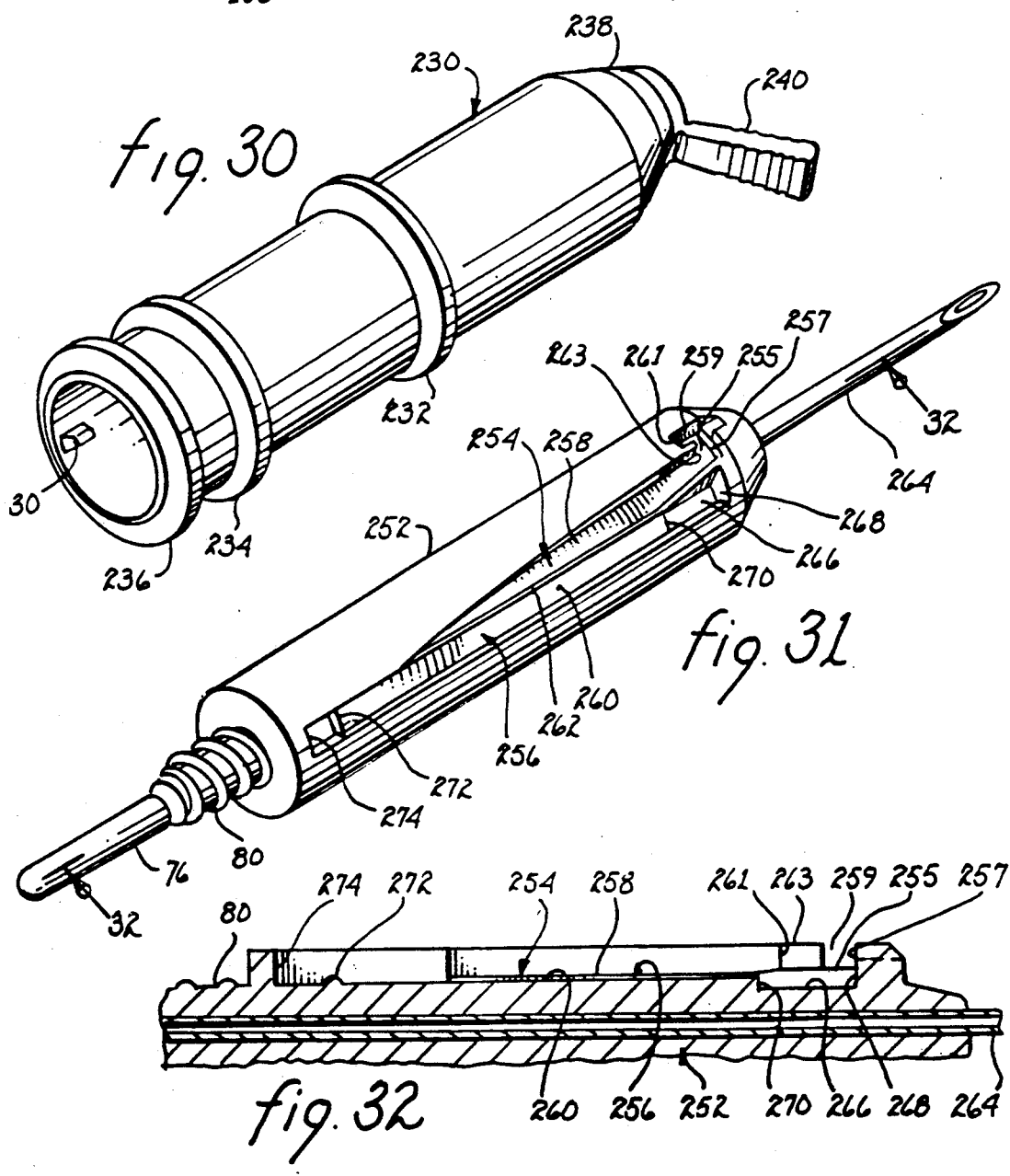
fig. 30
fig. 31
fig. 32

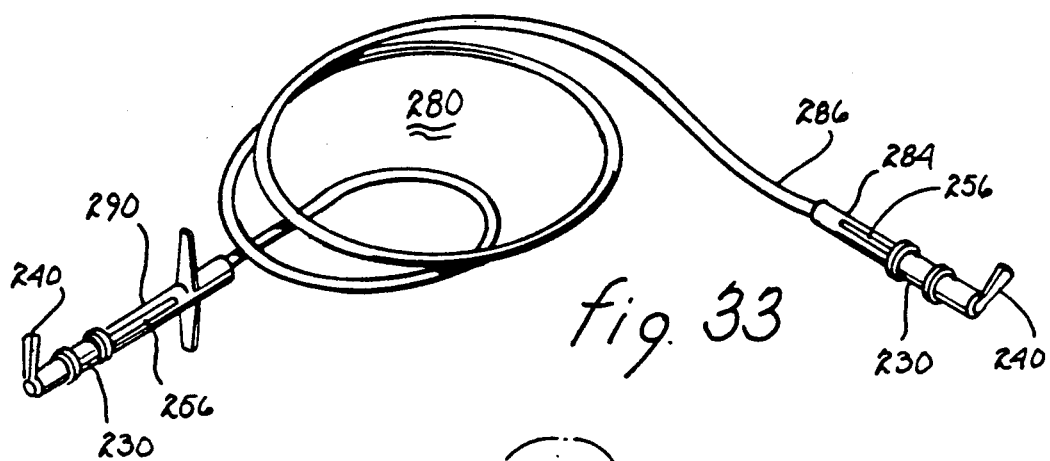
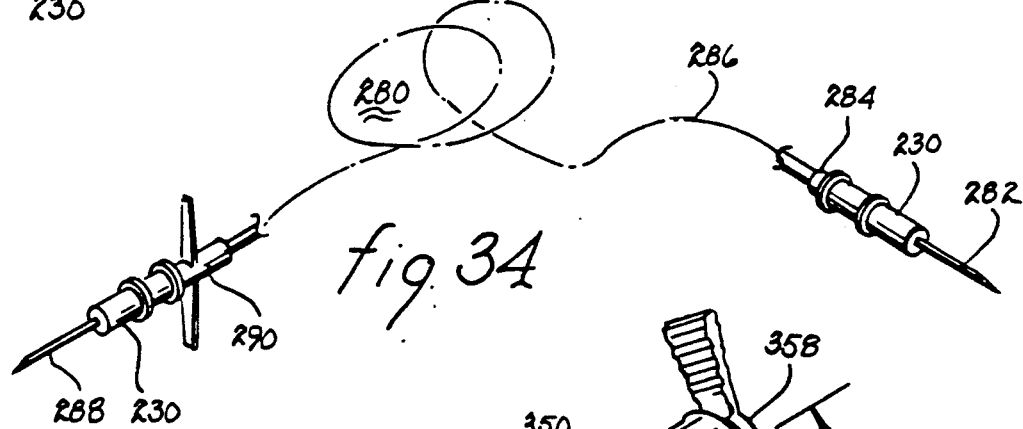
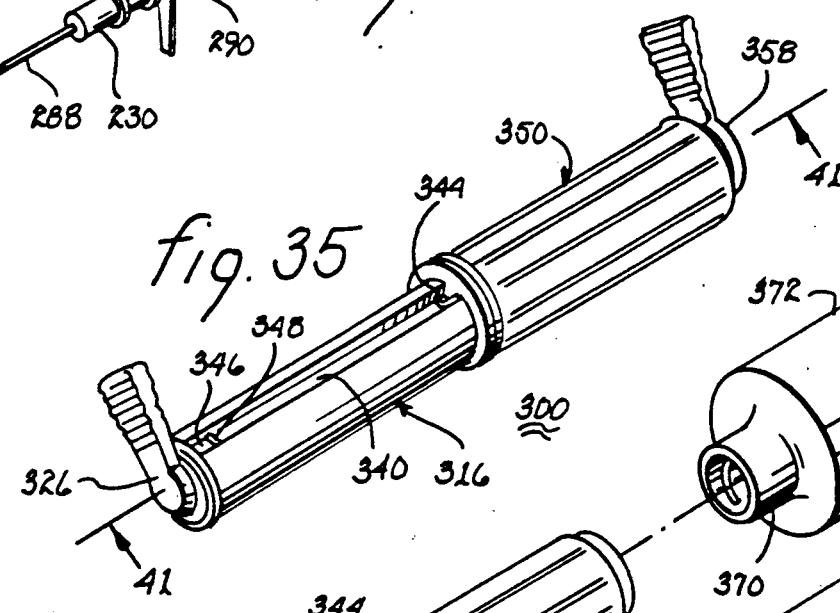
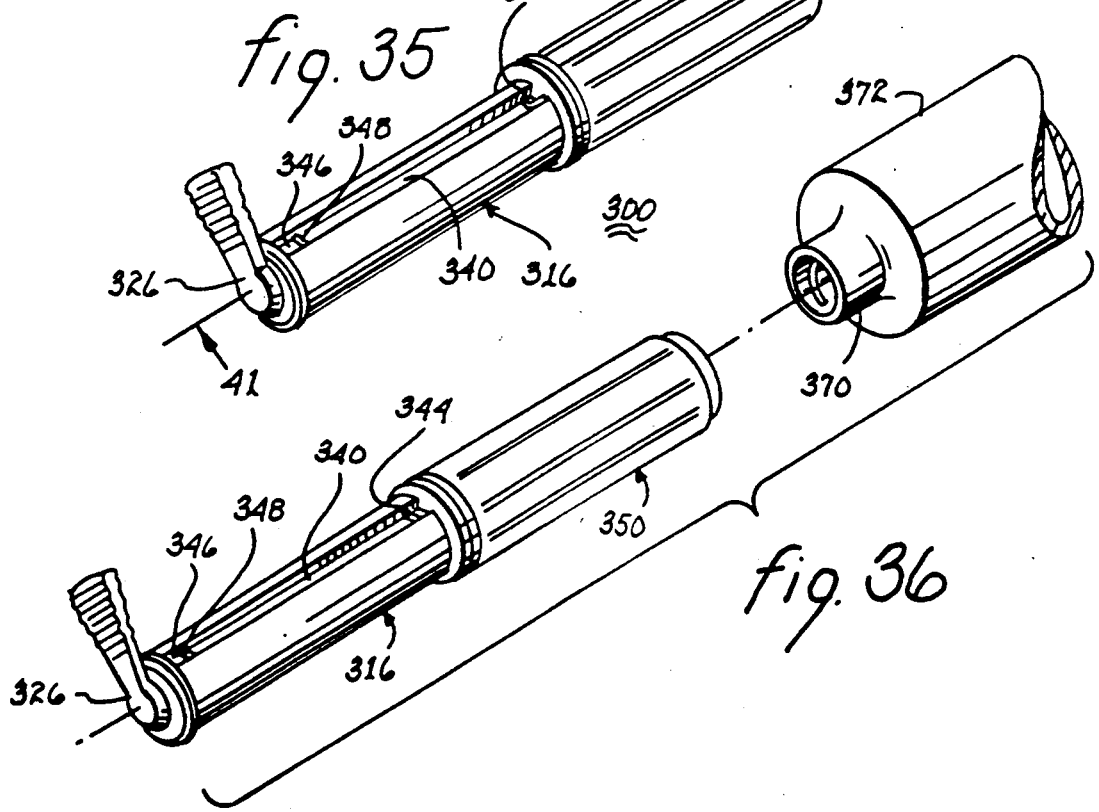

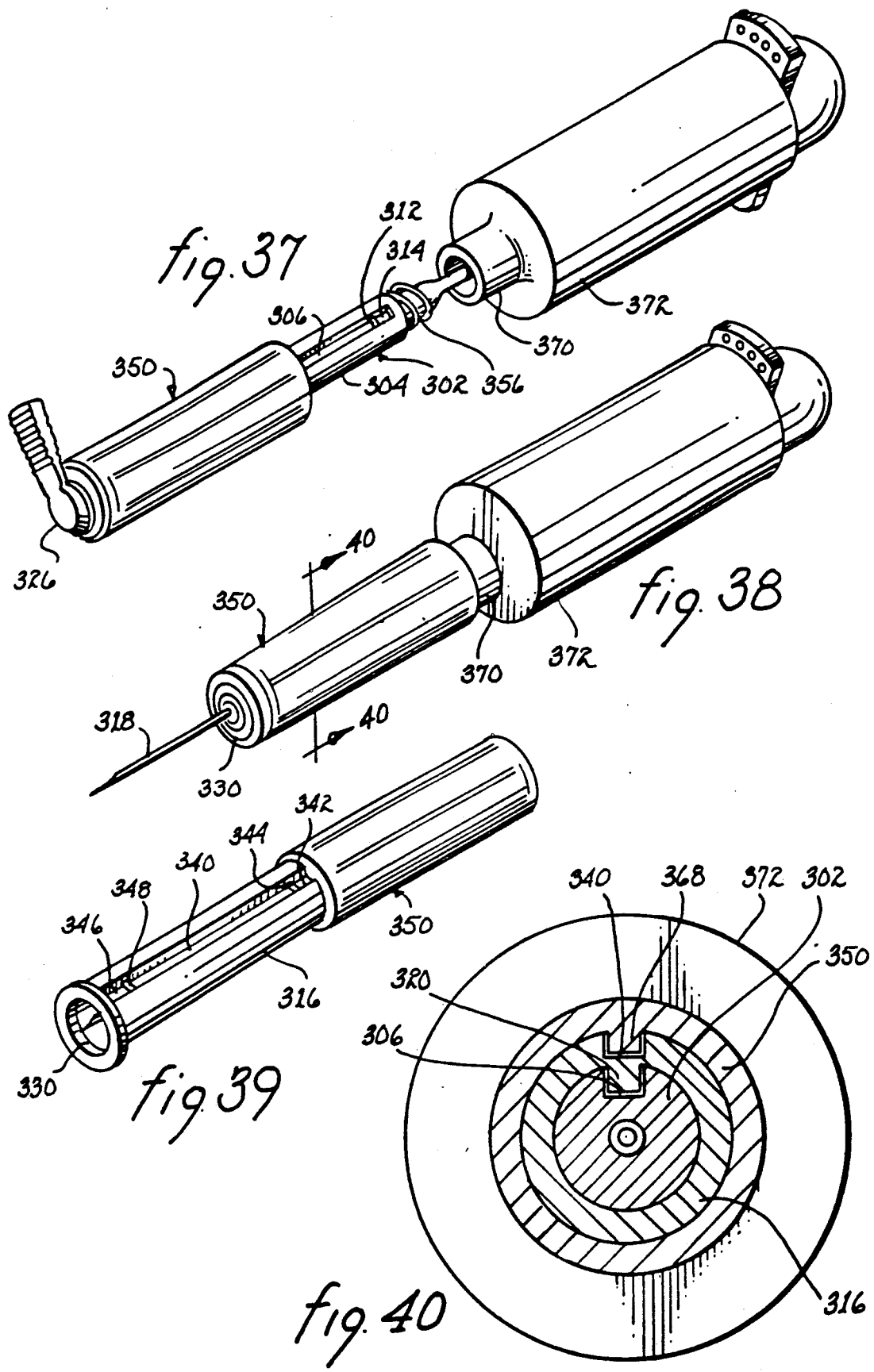

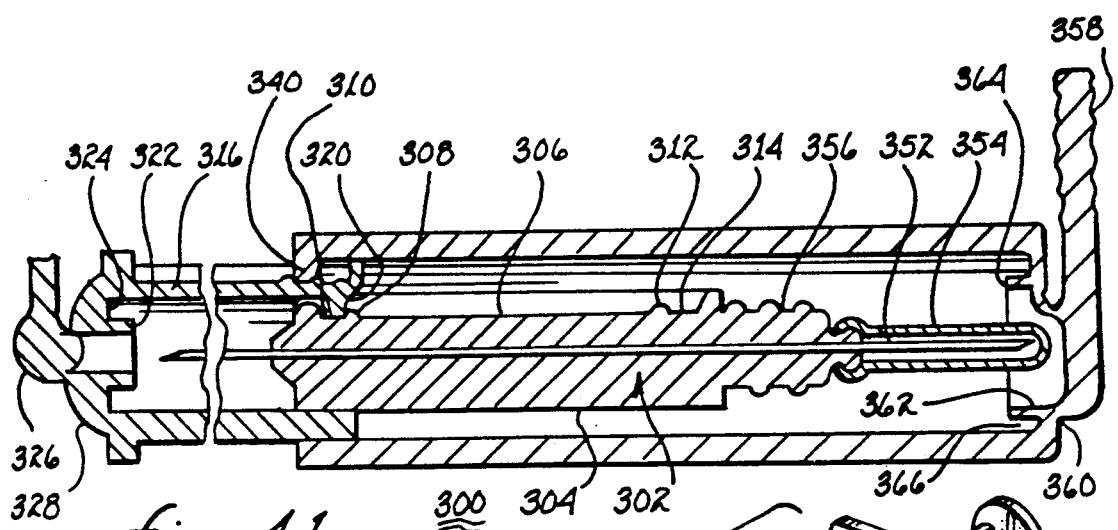
fig. 41
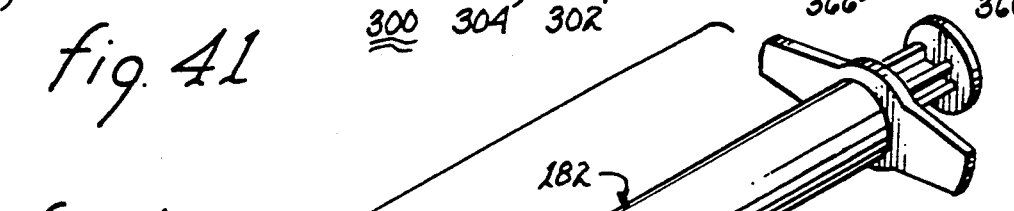
fig. 42
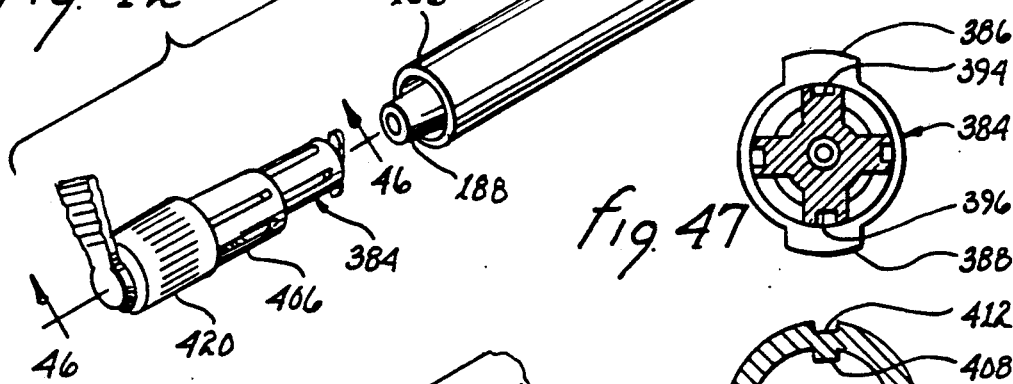
fig. 43
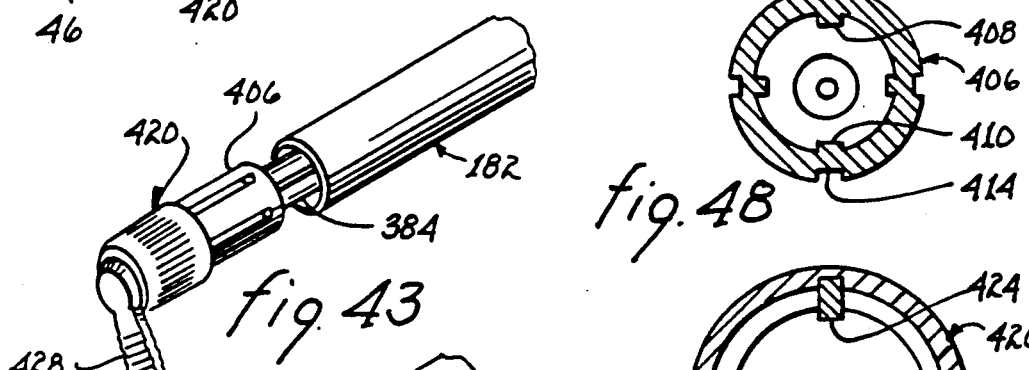
fig. 44
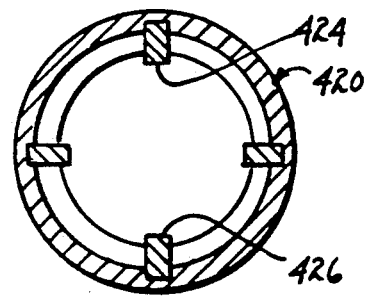

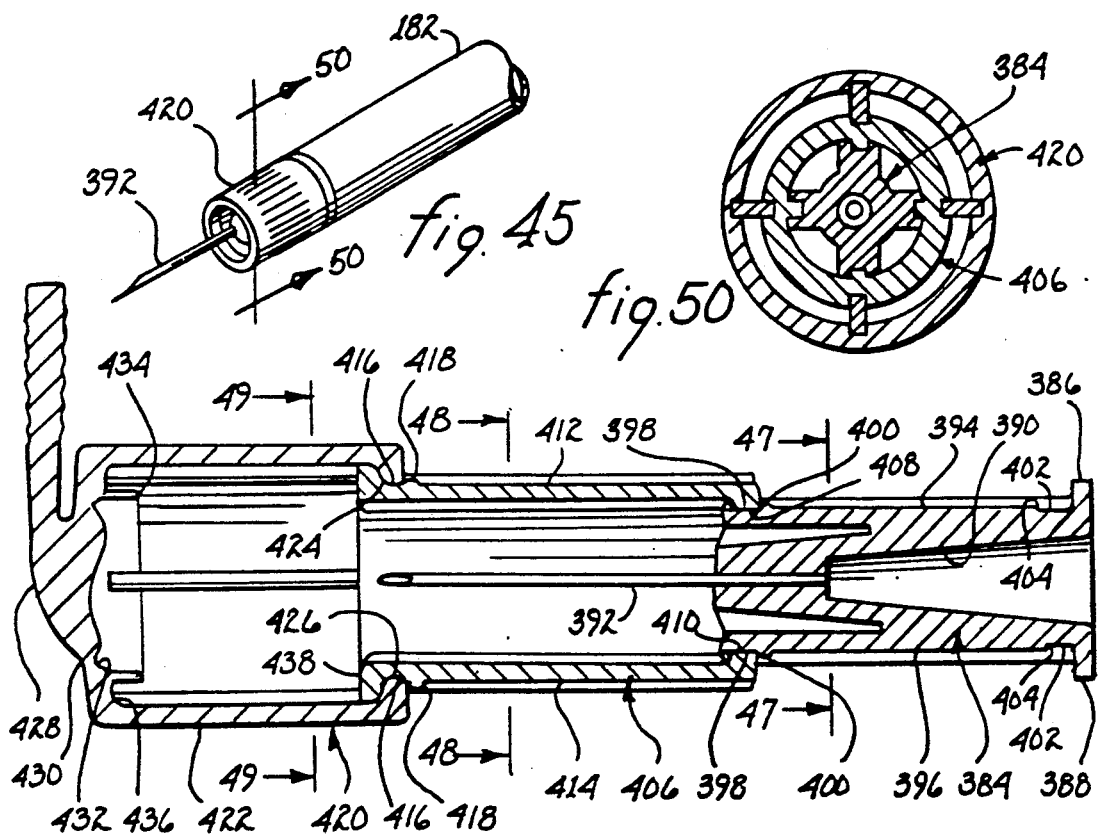
fig. 45
fig. 50
fig. 46
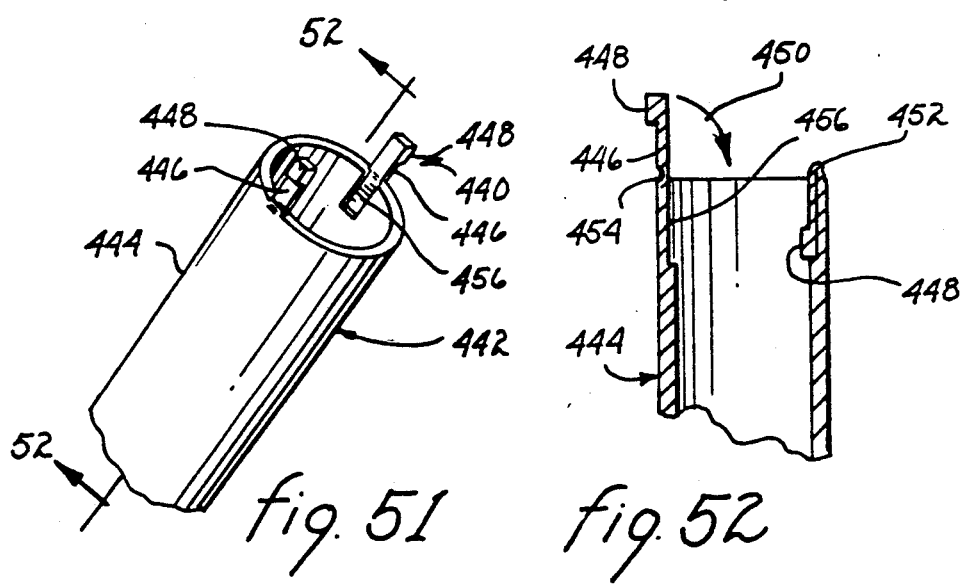
fig. 51
fig. 52

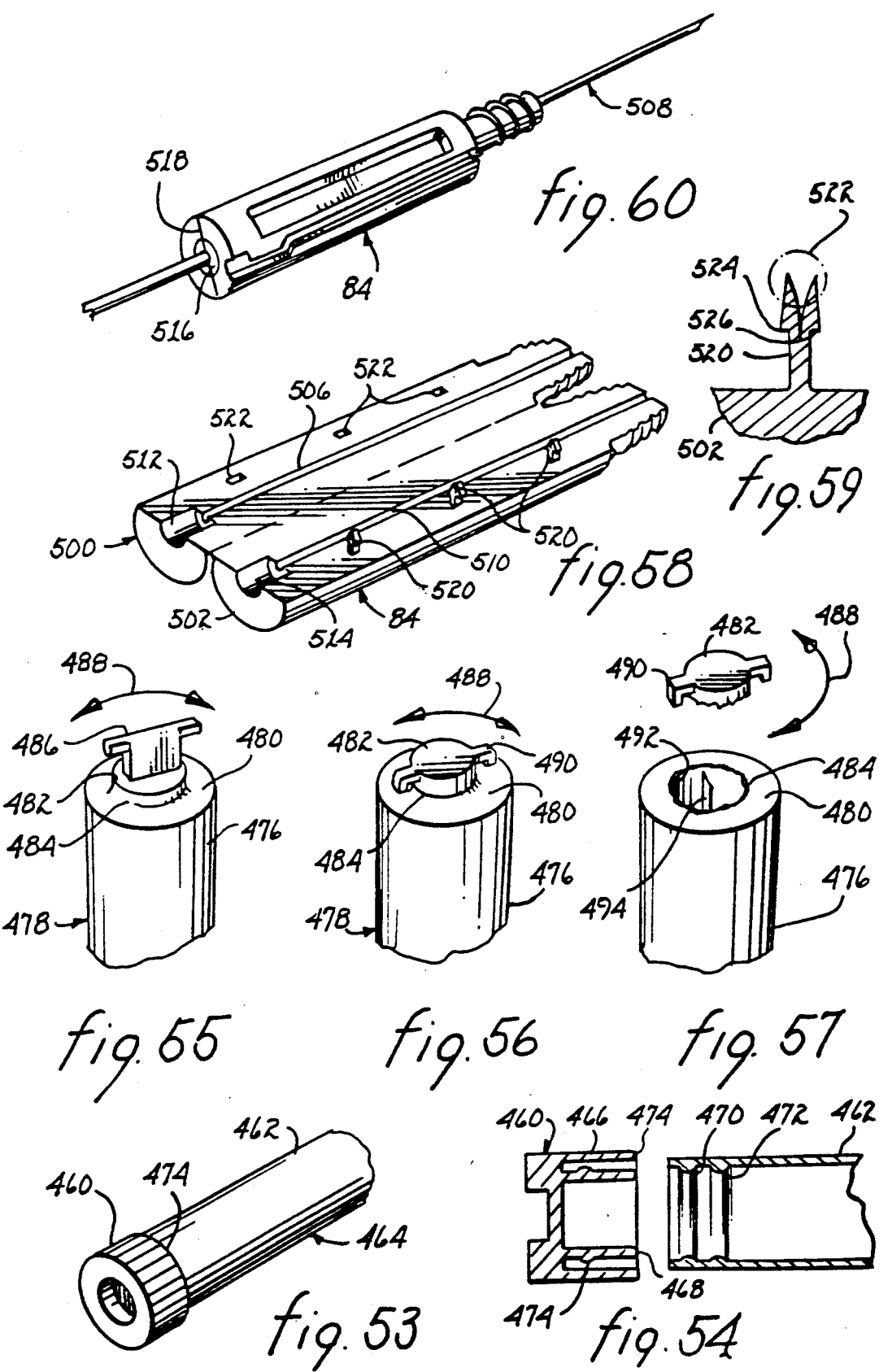

NEEDLE GUARD FOR BLOOD COLLECTION

This is a division of application Ser. No. 353,898 filed Apr. 13, 1989 of Alan S. Wanderer and William E. Sagstetter entitled "NEEDLE GUARD" (now abandoned), which is a continuation in part application of concurrently pending applications entitled "COMBINATION NEEDLE SHIELD/NEEDLE GUARD DEVICE POSITIVELY LOCKED ONTO DETACHABLE NEEDLE ASSEMBLIES FOR AN EVACUATED BLOOD COLLECTION SYSTEM AND HYPODERMIC SYRINGE" and "COMBINATION NEEDLE SHIELD/NEEDLE GUARD DEVICE FOR A HYPODERMIC SYRINGE WITH A PERMANENTLY ATTACHED NEEDLE", assigned Ser. Nos. 918,020, 919,373, filed on Oct. 14, 1986, Oct. 16, 1986, respectively (now U.S. Pat. No. 4,731,059 and 693,708 respectively).

BACKGROUND OF THE INVENTION

1. Field of the Invention

The present invention relates to a guard device for hypodermic needles and, more particularly, to guard devices for single and double ended needles.

2. Description of the Prior Art

A needle shield which must be removed from a needle hub before a syringe needle can be used for a medical procedure is described in each of U.S. Pat. Nos. 3,381,813, 3,934,722, 4,113,090 and 4,121,588. Each of these removable needle shields reveals several limitations, including: (1) after a liquid medicament has been drawn up in a syringe, medical personnel may occasionally delay the administration of the medicament, which delay requires retrieval and replacement of the needle shield to prevent contamination of the sterile needle and creates extra steps for busy medical personnel; (2) medical personnel often remove this needle shield by holding the needle shield between their teeth or lips. This practice has been associated with accidental self-puncture in the face or other bodily parts; (3) in order to re-cover a used needle with a previously removed needle shield, it is necessary to replace the needle shield back over the pointed end of the used needle, which replacement increases the risk to medical personnel of accidentally puncturing themselves with the pointed end of the used needle; and, (4) if the needle has been accidentally bent during a medical procedure or if the needle shield is replaced over the needle at an incorrect angle, the needle point may inadvertently pierce the side of the needle shield and puncture the fingers or hand.

Other U.S. Patents have issued which are directed to aspects of the present invention. U.S. Pat. No. 4,425,120 describes a needle guard for a removable needle which guard is attached to a syringe barrel. To remove the detachable needle from the syringe barrel, it is necessary to recover the used needle with a separate needle shield, which recovery increases the risk of puncture to medical personnel by the used needle point. In addition, the needle shield has an open end, which precludes sterility of the needle. U.S. Pat. No. 4,139,009 describes four longitudinal arms which are brought into lateral side-to-side contact with the intention of covering and protecting an enclosed needle. The front end of the cover and the lateral arms in side-to-side contact represent discontinuous locations which could permit microorganism penetration and contamination of the enclosed sterile needle. In addition, the arms in their normal unstressed condition are slightly bowed away from the longitudinal axis of the needle so that casual touching of the device could contaminate the needle through the interstices between the separated arms. When this device is pushed against a skin surface during the injection process, the arms must bow away from the longitudinal axis of the needle which bowing blocks visualization of the needle as it penetrates the skin and creates a hazard to the patient.

Various configurations of a double needle assembly are disclosed in U.S. Pat. Nos. 3,734,080 and 3,931,815, 2,460,641, 4,154,229, 4,295,476, 4,295,477, 4,312,362 and 4,340,068 for use in conjunction with evacuated blood collection systems and having removable needle shields.

With a double ended needle the risk of accidental contact with or puncture by either needle is substantially increased. In addition to the inherent danger from two potentially contaminated needles, other problems attendant a double needle blood collection system exist. For example, the needle engaging threads and lock (if used) of a normally reuseable container holder can become sufficiently worn to permit threaded disengagement during use. Such disengagement during the blood collection process exposes medical personnel to contact with or puncture by a potentially contaminated part of the posterior needle and the fluid being withdrawn. Withdrawal of blood in the blood collection process would also be interrupted. If the anterior needle is also inadvertently withdrawn, the potential for further exposure to contagious fluids exists.

After use, a single or a double ended needle assembly may contain, interiorly or exteriorly, a potentially infectious fluid which fluid may drip onto or otherwise come in contact with personnel, other equipment or a surface and pose a health hazard.

SUMMARY OF THE INVENTION

A needle guard for a hypodermic needle attached to a syringe barrel includes an axiallly translatable generally cylindrical sleeve slidably secured to the syringe barrel and having a removable tab at the proximal end for developing an aperture to accommodate exteriorization of the contained needle. A locking mechanism interconnects the syringe barrel with the distal end of the sleeve for fixating the sleeve and shielding the needle prior to and subsequent to removal of the tab. After removal of the tab a guide mechanism accommodates translation of the sleeve along the barrel to expose the needle for use; after use, the sleeve is slidable proximally to a locked position for receiving and containing the needle. All manipulation of the sleeve is from rearwardly of the needle to minimize the potential for accidental contact with the needle by medical personnel or other users of the hypodermic syringe. For double ended needles, an attached non-removable guard may be incorporated to extend over the anterior needle end and a further attached non-removable guard is extendable over the posterior needle end. Upon extension, either or both guards may be locked in place to prevent access to and further use of the potentially contaminated needle(s). To secure the double ended needle with the holder of a blood collection system, a further locking mechanism interconnecting the guard with the holder may be employed. A variant of the double needle assembly forming the present invention can accommodate an acute angular penetration of the blood vessel to be punctured despite a substantial girth that may be associated with the holder. Preferably, each needle guard, whether for a single or double ended needle, includes an annular trough for restraining outflow of fluid which may drip from the shielded needle. And, each needle guard is translatable between the retracted and extended position with one or two digits of one hand to leave free the other hand of a user.

It is therefore a primary object of the present invention to provide an attached non-removable needle guard for maintaining sterile a hypodermic needle prior to use and for guarding the hypodermic needle against inadvertent contact by a user after use.

Another object of the present invention is to provide a syringe barrel mounted non-detachable guard for a hypodermic needle extending from the barrel which guard is manipulatable from a location rearwardly of the hypodermic needle.

Still another object of the present invention is to provide a device positionally lockable about a needle of a hypodermic syringe to prevent inadvertent contact with the needle and any fluids dripping therefrom.

Yet another object of the present invention is to provide apparatus for protecting a user of a hypodermic syringe or hypodermic needle, whether single or double, against accidental transmission of blood borne infections, such as AIDS, hepatitis, syphilis and other infectious diseases through contact with the needle.

A further object of the present invention is to provide a double ended needle assembly having a guard for circumscribingly enclosing the anterior and posterior needle ends prior to and after use.

A still further object of the present invention is to provide a guard lockable in place to prevent reuse of a hypodermic needle.

A yet further object of the present invention is to provide apparatus for precluding inadvertent disengagement of the double ended needle from the container holder during use.

A yet further object of the present invention is to provide guards for each end of a double ended needle assembly which are operable independently and from a location posterior of the needle end to be enclosed.

A yet further object of the present invention is to provide a more shallow angle of access during blood withdrawal irrespective of the girth of the container holder or syringe barrel.

A yet further object of the present invention is to provide telescoping cylindrical segments of a needle guard which will allow enclosure of long needles without creating long and unwieldy needle assemblies.

These and other objects of the invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 illustrates a hypodermic syringe having an attached needle guard;

FIG. 2 illustrates the needle guard;

FIG. 3 is a partial cross-sectional view taken along lines 3—3, as shown in FIG. 2;

FIG. 4 is a cutaway view of the upper end of the hypodermic syringe illustrated in FIG. 1;

FIG. 5 is a partial cross-sectional view of the syringe barrel taken along lines 5—5, as shown in FIG. 4;

FIG. 6 is a further partial cross-sectional view of the syringe barrel taken along lines 6—6, as shown in FIG. 4;

FIG. 7 illustrates a step in the use of the present invention;

FIG. 8 illustrates a further step in the use of the present invention;

FIG. 9 illustrates the primary components of a blood collection system employing a double ended needle;

FIG. 10 illustrates a needle guard for a double ended needle;

FIG. 11 is a cross-sectional view taken along lines 11—11, as shown in FIG. 10;

FIG. 12 illustrates a needle guard protecting one needle end of a double ended needle prior to use of the needle;

FIG. 13 illustrates an exploded view of the double ended needle and needle guard;

FIG. 14 is a cross-sectional view taken along lines 14—14, as shown in FIG. 11;

FIG. 15 is a partial cross-sectional view taken along lines 15—15, as shown in FIG. 13;

FIG. 16 is a detailed view of the guide mechanism for the needle guard taken along lines 16—16 as shown in FIG. 13;

FIG. 17 is a cross-sectional view taken along lines 17—17, as shown in FIG. 16;

FIG. 18 is a cross-sectional view taken along lines 18—18, as shown in FIG. 16;

FIG. 19 illustrates further features of the guide mechanism for the needle guard;

FIG. 20 illustrates a part of a lock mechanism disposed upon and formed as a part of a container holder;

FIG. 21 is a cross-sectional view taken along lines 21—21, as shown in FIG. 20;

FIG. 22 is a detailed view illustrating the interconnection between a double ended needle and a container holder;

FIG. 23 illustrates an initial step in the operation of a needle guard for a double ended needle;

FIG. 24 illustrates a further step in the operation of a needle guard for a double ended needle;

FIG. 29 illustrates the needle guard in use with the detachable single needle variant;

FIG. 30 illustrates a variant of the needle guard;

FIG. 31 illustrates a variant of a double ended needle;

FIG. 32 is a partial cross-sectional view taken along lines 32—32, shown in FIG. 31;

FIGS. 33 and 34 illustrate apparatus embodying the present invention for withdrawing blood and delivery into a large sized container;

FIGS. 35, 36, 37, 38 and 39 illustrate the structure and operation of a telescoping variant of the present invention for a double ended needle;

FIG. 40 is a cross-sectional view taken along lines 40—40, as shown in FIG. 38;

FIG. 41 is a partial cross-sectional view taken along lines 41—41, as shown in FIG. 35;

FIGS. 42, 43, 44 and 45 illustrate the structure and operation of a telescoping variant of the present invention for a single needle;

FIG. 46 is a cross-sectional view taken along lines 46—46, as shown in FIG. 42;

FIG. 47 is a cross-sectional view taken along lines 47—47, as shown in FIG. 46;

FIG. 48 is a cross-sectional view taken along lines 48—48, as shown in FIG. 46;

FIG. 49 is a cross-sectional view taken along lines 49—49, as shown in FIG. 46;

FIG. 50 is a cross-sectional view taken along lines 50—50, as shown in FIG. 45;

FIG. 51 illustrates a variant of a key associated with a needle guard;

FIG. 52 is a cross-sectional view taken along lines 52—52, as shown in FIG. 51;

FIG. 53 illustrates a cap usable to seal the anterior end of the sleeve;

FIG. 54 is a cross-sectional view illustrating the mating structure between the cap and sleeve shown in FIG. 53;

FIG. 55 is a perspective view illustrating a variant pull off tab;

FIG. 56 is a perspective view illustrating another variant of the pull off tab;

FIG. 57 is a perspective view illustrating the removed variant shown in FIG. 56;

FIG. 58 illustrates a manner of manufacturing a double ended needle body, such as that illustrated in FIG. 13;

FIG. 59 illustrates a prong usable to maintain the double needle body halves illustrated in FIG. 58 is joined relationship;

FIG. 60 illustrates the joined configuration of the double ended needle body halves illustrated in FIG. 58;

DETAILED DESCRIPTION OF THE PREFERRED EMBODIMENT

Figure 25:
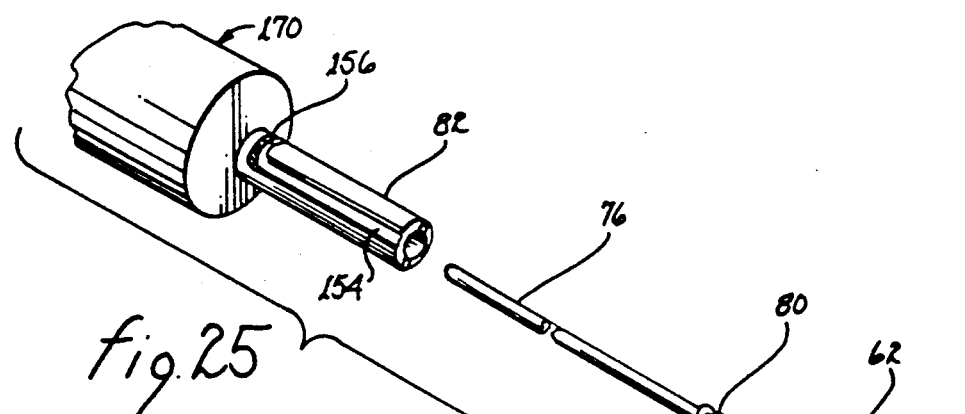
FIG. 25 illustrates a needle guard usable with a variant of a double ended needle.

Referring to FIG. 1, there is shown a hypodermic syringe 10 having a barrel 12 and a needle 14. The needle may be attached to or detachable from the barrel. A needle guard 16 is secured to proximal end 18 of barrel 12. The needle guard serves the function of preventing injury and injection from the needle to a user or damage to the needle; it may also serve the function of maintaining the needle sterile.

Needle guard 16 includes a sleeve 20 of an internal diameter to concentrically and snugly, but slidably receive barrel 12. Preferably, the sleeve is of transparent or translucent material to permit view of any graduations 21 upon the barrel of the fluid level within the syringe.

As shown in FIGS. 2 and 3, proximal end 22 of needle guard 16 includes a tab 24 extending thereacross in sealed relationship. A handle 26 is formed as part of the tab. An annular weakened zone, represented by numeral 28 is formed as part of the tab and serves as a weakened junction between the tab and proximal end 22. As illustrated in FIG. 7, a pull on handle 26 will fracture and sever tab 24 from proximal end 22 along annular zone 28 to sever the tab from needle guard 16 and develop an aperture 48 through which the needle may protrude. A key 30 extends radially inwardly from inner surface 32 of sleeve 20. The key may be rectangular in planform and undercut on all four sides, as illustrated; other configurations of the key are contemplated. An inwardly radially extending ridge 29 may be formed in the interior of proximal end 22 to serve as a dam an discourage outflow of any fluids dripping from the needle outside the guard.

Referring jointly to FIGS. 4, 5 and 6, the structure attendant barrel 12 for receiving/engaging key 30 to regulate and control movement of needle guard 16 relative to the barrel and needle 14 will be described. A tapered longitudinally oriented channel 32 extending radially at proximal end 18 receives key 30 of needle guard 16 for the purpose of mounting the needle guard upon barrel 12. The recess includes a step 33 from channel 32 to prevent passage of the key back into the channel. The channel leads to a recess 34 for nestingly receiving key 30. An annular channel 36 extends from recess 34. Sides 38, 40 at the junction between recess 34 and channel 36 may be necked down to serve as a constraint against passage of key 30 from the recess to the channel. A longitudinal channel 42 extends from channel 36 for a distance equivalent to the distance through which needle guard 16 is to be translated. A recess 44 is disposed at the terminal end of channel 42. Passage of key 30 into recess 44 may be restrained by a ridge 46 extending across the floor of channel 42 and defining one end of the recess. Channels 36 and/or 42 and the channels to be described hereafter may be undercut to lock key 30 therein.

FIGS. 7 and 8 illustrate the operation of needle guard 16 with respect to barrel 12 to uncover and recover needle 14. When syringe 10 is to be used, handle 26 of tab 24 is pulled to sever the tab from proximal end 22 of the needle guard 16. The severance produces and aperture 48 at the proximal end to permit protrusion of needle 14 therethrough. In the initial position of the needle guard, key 30 is disposed in recess 34, which recess prevents/restrains both longitudinal and rotational movement of the needle guard with respect to the barrel. After aperture 48 has beeen formed, needle guard 16 is grasped by an operator, preferably from a location rearwardly of the needle, and the needle guard is rotated counterclockwise. The resulting rotational movement causes key 30 to enter annular channel 36 past the restraint effected by necked sides 38, 40. Thereafter, translation by manipulation of the needle guard toward the distal end of syringe 10 will draw the needle guard along barrel 12 until key 30 becomes lodged within recess 44 at the end of channel 42 after having been forced past ridge 46. In this position, particularly illustrated in FIG. 8, needle 14 is fully exposed and the syringe is ready for use. If the needle guard is translucent or transparent, medical personnel operating syringe 10 will be able to note any graduations 21 upon barrel 12 and the level of fluid therein.

After use of the syringe for its intended purpose and to protect medical personnel against inadvertent contact with needle 14, needle guard 16 is grasped, preferably from a point rearwardly of needle 14, and slid forwardly with sufficient force to overcome the restraining effect of ridge 46 upon key 30. Upon full extension of the needle guard, it is rotated clockwise to place key 30 in annular channel 36 and ultimately force the key into recess 34 past the restraining effects of sides 38, 40. The needle guard will again be in the position illustrated in FIG. 7. In this position, the needle guard serves in the manner of a shield to prevent inadvertent contact with needle 14. Thereby, transmission of any infectious diseases by any fluids in or about the needle will be avoided. Moreover, the dam provided by annular ridge 29 (see FIG. 3) serves to contain outflow from within the needle guard of any fluid which may have dripped from needle 14.

It may be noted that the function and purpose of channel 32 is that of initially engaging needle guard 16 with barrel 12. Furthermore, if a particular need arises, the needle guard can be disengaged from the barrel by forcing key 30 out of recess 34 and into channel 32. Further longitudinal movement of the needle guard will result in disengagement of the key with channel 32. It may be further noted that syringe 10 may be used without needle guard 16 or such a needle guard may be added to barrel 12 by a user when circumstances warrant.

The purpose of tab 24 is that of enclosing a needle to locate the needle within an enclosure which will permit and accommodate maintaining the needle sterile. It is therefore conceivable that for many reasons, such as manufacturing ease, selection of materials, production cost and/or ease or use, means other than tab 24 for sealing the end of sleeve 20 may be employed without departing from the purpose and function of the tab. Accordingly, the previous and following discussion of the tab, such as tab 24, is for the purpose of identifying the best mode presently contemplated as a sealing means for the end of the sleeve but other configurations may be incorporated for any or all of the reasons stated above. In example, a snap fit tab or cap which will sealingly engage, in the manner of a concentric shroud, the proximal end of the sleeve and maintain sterility of the enclosed needle may be incorporated. Removal of such tab or cap to develop the aperture through which the enclosed needle can be exteriorized can be by a twist off action or a direct pull action.

Blood collection apparatus having a variant 62 of needle guard 16 for use with a double ended needle 64 is illustrated in FIG. 9. The double ended needle mates with container holder 66 to locate therein the posterior needle 78 of double ended needle 64. An evacuated collection tube 68 includes a rubber stopper 70. To collect blood, the collection tube is forced into container holder 66 until the posterior needle penetrates stopper 70 and blood will be drawn into the collection tube 68.

Details of double ended needle 64 and guard variant 62 will be described with joint reference to FIGS. 10–15. Prior to use, double ended needle 64 is enclosed within guard variant 62 disposed generally about the anterior needle and a shield 72 generally disposed about the posterior needle. A tape 74 circumscribingly engages the mating ends of the guard variant and shield to seal and to maintain sterile the enclosed double ended needle. Upon removal of tape 74, shield 72 may be disengaged from about double ended needle 64. The exposed portion of the double ended needle includes a posterior needle sheathed within a flexible sheath 76. The purpose of sheath 76 is to maintain enclosed posterior needle sterile prior to penetration by the needle of stopper 70. Sheath 76 also functions as a valve to recover the posterior needle after removal of a collection tube 68, so that the user can attach a second or more collection tubes to collect multiple blood samples. This is, upon insertion of collection tube 68 within container holder 66, the stopper will bear against the needle to force penetration of sheath 76 by the needle and subsequent penetration of stopper 70. Upon withdrawal of collection tube 68 within the container holder, the resulting disengagement with the posterior needle will permit the sheath to extent and again enclose the needle. Hub 80, from which posterior needle 78 extends and to which sheath 76 is attached, is in threadable engagement with threads of boss 82 of container holder 66. In this manner, the double ended needle is secured to the container holder.

Body 84 of double ended needle 64 may include a plurality of longitudinal ridges 86, as illustrated, to assist in manipulation. An adjacent pair of parallel longitudinally aligned flanges 88, 90 define a channel 92 extending longitudinally along body 84. These flanges, in combination with ridges 86, provide support and guidance for guard variant 62, as illustrated particularly in FIG. 14, during translation along body 84. Guard variant 62 includes a cylindrical section 94 terminated at proximal end 96 by a tab 98 having a handle 100. An annular weakened zone 102 joins tab 98 with proximal end 96. Upon removal of the tab by pulling upon handle 100, the tab will severed essentially along zone 102 to produce an aperture 104 at proximal end 96. A cylindrical ridge 106 is disposed at proximal end 96 to define, in combination with cylindrical section 94, an annular trough 108. A key 30 extends radially inwardly from interior surface 110 of cylindrical section 94. The key may be undercut, as illustrated by the dashed line in FIG. 15.

Referring primarily to FIGS. 16 to 19, the interconnecting relationship between guard variant 62 and double ended needle 64 of guard variant 62 will be described. Guard variant 62 is brought into mating relationship with body 84 by locating key 30 into and past threshold channel 120 to a first position in guide channel 122 defined by end wall 124, side wall 126, barrier 128 and restraining means, such as ridge 130. In this position, key 30, and hence guard variant 62, will be inhibited from rotational movement with respect to body 84 and longitudinal movement toward anterior needle 112 by end wall 124 and restrained against movement in the other direction by ridge 130.

To prevent inadvertend disengagement between guard variant 62 and double ended needle 64 through traverse of key 30 over end wall 124, it is perferable to have the end wall extend radially outwardly as far as possible and yet permit mounting of the guard variant upon the body. If the material of which end wall is fabricated is resiliently compressible, accommodation of the key therepast through compression of the end wall will permit a higher or radially outwardly extending end wall than otherwise. Such radially extended sidewall will also tend to inhibit to a greater degree inadvertent disengagement between the guard variant and the needle body.

When anterior needle 112 is to be exposed, tab 98 is pulled away to form aperture 104. Guard variant 62 is gripped and pulled longitudinally toward posterior needle 78. The force of such a pull will cause key 30 to ride over ridge 130. Simultaneously, sidewall 126 will guide the key into channel 92, which channel extends longitudinally along body 84. To reenclose anterior needle 112 within guard variant 62, the guard variant is translated longitudinally along body 64 with key 30 riding in channel 92. Translation will occur until the key comes to a stop against end wall 132. Upon rotation of the guard variant in a clockwise direction, the key will ride over sloping side 134 of flange 136 and into recess 138. Rotation in the other direction of guard variant 62 will be precluded by vertical wall 140 of flange 136. The walls of the recess, in combination with flange 136 will preclude either longitudinal or lateral movement of guard variant 62. Without the capability of any further movement, further exposure, and hence use, of anterior needle 112 is precluded.

To secure body 84 with boss 82 of container holder 66, a detent mechanism may be employed to preclude inadvertent unthreading of hub 80 with boss 82. Diametrically opposed detents 142, 144 extending longitudinally from end 146 mate with equivalently located slots 148, 150 in end surface 152 of boss 82. A longitudinally aligned channel section 154 is formed in boss 82. A circumferentially (annuarly) extending channel 156 interconnects with channel section 154 at its terminal end. Restraining means, such as a ridge 158, extends across channel 156 to define a recess 160 at its terminal end. Upon threaded engagement of hub 80 with boss 82, channel 92 in body 84 will be aligned with channel section 154 of the boss. Alternatively, annular channel 156 may be omitted and ridge 158 may be located thereacross to serve as a restraint against disengagement between boss 82 and guard variant 62.

When guard variant 62 is to be longitudinally translated to expose needle 112, key 30 is guided from guide channel 122 into channel 92 and into channel section 154 to its terminal end. Subsequent counterclockwise rotation of the guard variant will translate key 30 into channel 156 to recess 160. Because of ridge 158, movement of the key out of recess 160 will be restrained. The translatory movement of guard variant 62 is particularly illustrated in FIGS. 23 and 24 with the resulting effect of exposing anterior needle 112. It may be pointed out that by appropriate dimensioning of the guard variant, cylindrical ridge 106 (see FIG. 15), may be dimensioned to bear against end 162 of body 84 when key 30 is engaged with channel 156 at location 158 of boss 82. Such engagement in combination with the engagement of location 158 will provide a mechanical restraint against inadvertent and potentially unfortunate results should double ended needle 64 become disengaged from container holder 66. Accordingly, a positive lock to maintain the double ended needle in place can be provided by guard variant 62.

FIG. 21 illustrate a hub 82 of container holder 66 having a pair of diametrically opposed circumferentially oriented channels 156, including respect ridges 158. The purpose of this figure is to suggest the use of a pair of diametrically opposed keys in guard variant 62 with a pair of diametrically opposed channels 92 in body 84 along with guide channels 122. Such duality may provide a more stable apparatus for locating and guiding the guard variant.

Figure 26:
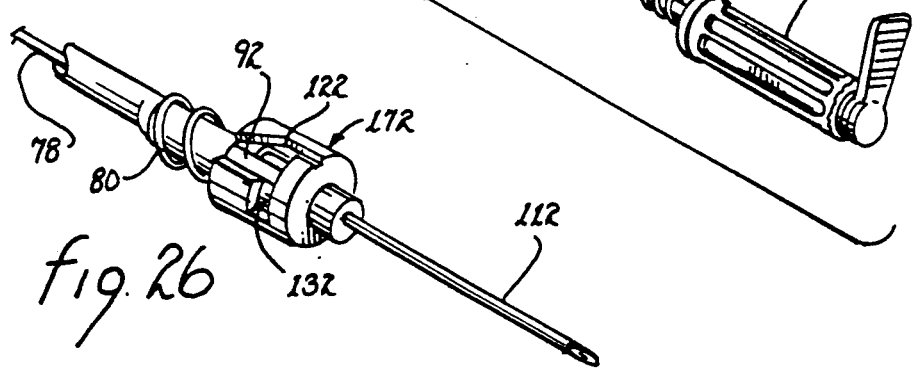
FIG. 26 illustrates the configuration of the double ended needle variant.
Figure 27:
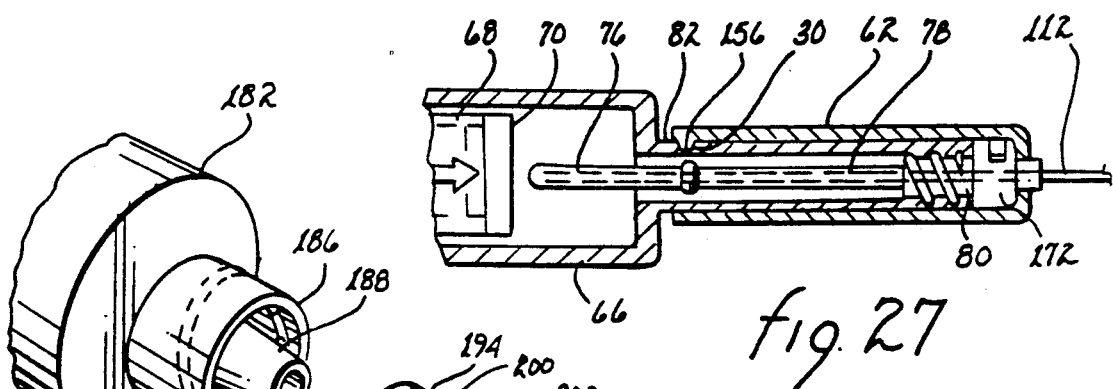
FIG. 27 is a cross-sectional view illustrating the double ended needle variant in use.

Referring jointly to FIGS. 25, 26 and 27 there is illustrated a variant 170 of container holder 66 and an accompanying variant 172 of body 84 (FIG. 13) of double ended needle 64. With this and other variants disclosed, the preferred needle angle access may be achieved even with large girth container holders due to the resulting longitudinal displacement of the container holder. Boss 82 is substantially extended longitudinally and includes an equivalently extended channel section 154. This channel section terminates in a channel 156, as described with reference to FIG. 20. Body variant 172 includes guide channel 122 as described above along with a section of channel 92 with its terminating recess 132. Hub 80 supports posterior needle 78 which has been substantially lengthened in portion to boss 82. This needle is terminated by a flexible sheath 76, as discussed above. Guard variant 62, as described above is mechanically and operatively engaged with body variant 172 as it is with body 86. A shield, like shield 72 shown in FIG. 11, may be employed to house and protect posterior needle 78 and its enclosing sheath 76. The attachment of body variant 172 of the double ended needle with boss 82 is as described above. Similarly, the translatory movement of guard variant 62 to uncover and recover anterior needle 112 is as described above.

Figure 28:
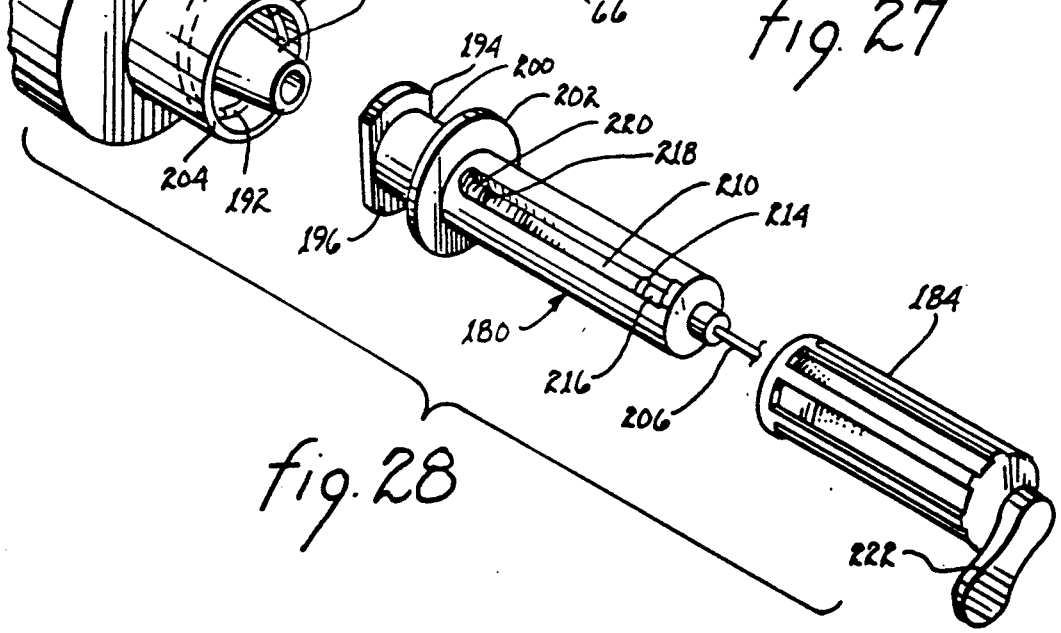
FIG. 28 illustrates a needle guard for use with a variant of a detachable single needle.

Referring jointly to FIGS. 28 and 29 there is shown a variant 180 of a single needle detachably attachable to a hypodermic syringe 182 and including a needle guard variant 184. The hypodermic syringe includes a cylinder 186 circumscribing a hub 188. Interior surface 190 of the cylinder includes a helical ridge 192, or thread, for threadedly securing variant 180 to the hypodermic syrings, such as with a Luer lock.

The single needle variant includes a pair of diametrically opposed dogs 194, 196 for engaging helical ridge 192 to threadedly secure single needle variant 180 with the hypodermic syringe. Upon such threaded engagement by dogs 194, 196, hub 188, which is cone shaped, penetrably engages and sealingly mates with a similarly cone shaped recess 198 within cylindrical section 200 of single needle variant 180. An annular flange 202 is located with respect to cylinder 200 to contactingly engage end 204 of cylinder 186 upon mating engagement of hub 188 with recess 198. Unnecessary over-tightening of the pressure fit Luer lock is prevented by contact of annular flange 202 with end 204; thereby, a constant tightening pressure upon the Luer-lock is provided. As particularly illustrated in FIG. 29, upon such engagement, fluid communication between needle 206 and passageway 208 through hub 188 is established.

Guard variant 184 includes a key 30, which may be of the shape and configuration discussed above, extending radially inwardly from the interior of cylindrical section 94. A longitudinally aligned channel 210 is disposed in body 212 of single needle variant 180 to receive and accommodate translation therealong of key 30. Restraining means, such as ridge 214 is disposed across the channel proximate the anterior end of the channel to define a recess 216. A similar ridge 218 is disposed across the channel proximate the posterior end to define a recess 220. These ridges serve to restrain movement of key 30 out of the respective recess unless a substantial force applied longitudinally to guard variant 184 occurs. Accordingly, the guard variant will normally be and remain located in a position to maintain needle 206 covered or uncovered.

Guard variant 184 includes a tab 222, which may be like tab 98 described above. Furthermore, the guard variant may include an annular trough, such as trough 108 illustrated in FIG. 15 and described above. Aperture 224, formed in the proximal end of guard variant 184 upon removal of tab 222 may be sized to accommodate penetration of boss 226 supporting needle 206.

FIG. 30 illustrates a variation in the external configuration applicable to any one of the needle guards discussed above. Further variant 230 of a needle guard includes one or more annular flanges, such as any or all of flanges 232, 234 and 236. The purpose and function of these flanges is to permit medical personnel to use with facility, only one or two digits of one hand to engage and effect translatory movement of the guard. This will free the other hand for associated or related functions, such as administering a medication or drawing blood. Depending upon dimensional considerations, key 30 may be disposed adjacent the posterior end of the guard variant, as illustrated in FIG. 30, or further longitudinally forwardly therefrom, as illustrated previously. Anterior end 238 of the guard variant may be cone shaped to better define or more easily define the annular weakened zone which defines the aperture to the guard variant upon removal of tab 240. Moreover, an interior cone shaped anterior end, whether or not an annular trough is disposed therein, will tend to discourage outflow of any fluids dripping from the needle enclosed within the guard variant after the needle has been used.

FIGS. 31 and 32 illustrates a further variant 250 of body 252 supporting the double ended needle. Guide channel 254 is essentially straight and defines a relatively shallow angle with respect to longitudinal channel 256. The resulting reduction in rotation rate of an engage guard with respect to longitudinal movement of the guard is somewhat more preferable to a user. It may be noted that the floor or base 258 of the guide channel is somewhat outwardly radially displaced from base 260 of longitudinal channel 256 to form a lip 262 along the line of demarcation therebetween. This lip will discourage, if not prohibit, translation of key 30 of a needle guard from the longitudinal channel into the guide channel during recovering of anterior needle 264. The anterior end of guide channel 254 includes a receiving recess 255 defined by a cut down end wall 254, a side wall 259, a further end wall 261 and a longitudinally aligned wall 263. After passage of a key 30 across end wall 257, the key will be retained within the receiving recess by the tree sides and wall defining the receiving recess. More specifically, an inadvertently applied force having a longitudinally oriented component and applied to a mounted needle guard will not cause the needle guard to be displayed longitudinally due to the interference with key 30 presented by further end wall 261. To obtain translation of key 30 (and the needle guard) within and along guide channel 254, the needle guard will have to deliberately translated anteriorly and then rotated (clockwise) to pass key 30 past longitudinal wall 263 and into the anterior end of the guide channel.

The anterior end of longitudinal channel 256 includes a recess 266 defined by end wall 268 and step 270. This end wall and step will preclude longitudinal translation of key 30 when the latter has been pushed into recess 266. The posterior end of longitudinal channel 256 includes restraining means, such as ridge 272 extending across base 260. The ridge, in combination with end 274 provides a detent function to maintain an interacting guard in the retracted position. A hub 80 is formed at the posterior end of body 252 to support a posterior needle enclosed within sheath 76.

Apparatus 280 for drawing blood from a patient and into a large volume container is illustrated in FIGS. 33 and 34, which apparatus incorporates one of the needle guards described above along with its advantages. A needle 282 is secured to and extends from a body 284. The needle, through the body, is in fluid communication with a length of conduit 286. A second needle 288 is secured to and extends from a second body 290; this needle, through the body, is also in fluid communication with conduit 286. A needle guard, such as guard variant 230 illustrated in FIG. 30, is in engagement with body 284. The engagement means may include guide channel 254 and longitudinal channel 256 of the configuration illustrated in FIG. 31. Similarly, the guard associated with needle 288 and body 290 may be like guard variant 230 illustrated in FIG. 30. The means disposed in body 284 for engaging and regulating translation of the associated guard variant may also include guide channel 254 and longitudinal channel 256, as illustrated in FIG. 31.

In operation, needles 282 and 288 are covered by the respective guard variant 230 prior to use. To use apparatus 280, needle 282 is exposed by pulling on tab 240 to permit exteriorization of the needle by translatory movement of guard variant 230. Thereafter, the needle is inserted in a patient's blood vessel. Needle 288 is exteriorized from guard variant 230 by pulling on tab 240 and translating the guard posteriorly along body 290. Needle 288 is subsequently inserted through the stopper of a container for receiving the bood withdrawn. On completion of the procedure, each guard variant is translated anteriorly to recover the associated needle to protect medical personnel against inadvertent contact with either of the needles and any fluid that might drip therefrom.

Referring jointly to FIGS. 35 to 41, a telescoping double guard assembly 300 for a double ended needle 302 will be described. Body 304 includes a longitudinally oriented channel 306 having restraining means, such as ridge 308 disposed distal to the anterior end of body 304 to define a first location 310. Further restraining means, such as ridge 312 defines a second location 314 proximate the posterior end of body 304. Needle guard 316, disposed at the anterior end of the body to cover anterior needle 318, includes a key 320 extending radially inwardly for translatable engagement with channel 306. The guard may include a cylindrical ridge 322 for defining an annular trough 324. A tab 326 is removably attached to the guard via an annular weakened zone 328. Upon pulling on tab 326, the tab will be severed along the line of the zone to develop aperture 330 for penetrable engagement by needle 318. Guard 316 is translatable from first location 310 to second location 314 and return. However, ridges 308 and 312 restrain translation out of each respective location to prevent inadvertent or unwanted translation and concomitant uncovering/covering of needle 318.

Needle guard 316 includes a longitudinally oriented channel 340 disposed in the peripheral surface of the needle guard. The posterior end of channel 340 includes a first location 342 defined by restraining means, such as ridge 344. A second location 346 is disposed at the anterior end of channel 340 and is defined by restraining means, such as ridge 348. A needle guard 350 extends posteriorly over body 304 to enclose and cover posterior needle 352 and its associated sheath 354 along with hub 356. A tab 358 is disposed at the posterior end of needle guard 350. The tab is secured to the needle guard via a weakened annular zone 360. Upon pulling on tab 358, it will sever from needle guard 350 along zone 360 to define an aperture 362. A cylindrical ridge 364 may encircle aperture 362 and define an annular trough 366.

A key 368 extends radially inwardly within needle guard 350 for engagement with channel 340. Translatory movement of needle guard 350 from first location 342 to second location 346 is restrained by the respective ridges. Thereby, needle guard 350 will tend to remain positioned relative to needle guard 316 unless an external force of a certain magnitude is applied to cause disengagement or repositioning of key 368 from the first or second locations. In operation, tab 358 is severed from needle guard 350; upon such severance, translation of the needle guard from the first location to the second location and into concentric overlap with needle guard 316 will uncover needle 352 enclosed within sheath 354, as illustrated in FIG. 37. Threaded engagement of hub 356 with boss 370 of container holder 372 may be effected by rotationally manipulating double ended needle assembly 300 by gripping and rotating relocated needle shield 350. It may be noted that translation of needle guard 350 may be from a position rearwardly of posterior needle 352 to avoid inadvertent contact with or puncture by the needle.

Once hub 356 is threadedly secured to the container holder, tab 326 is severed from needle guard 316. In the position illustrated in FIG. 37, needle guard 350 has been placed in its second location, as discussed with respect to FIG. 41. Upon application of a pulling force upon needle guard 350, key 320 of needle guard 316 will be translated from first location 310 along channel 306 to second location 314. This position is illustrated in FIG. 38. Commensurate therewith, anterior needle 318 will have penetrated through aperture 330 and become exposed. The manipulation of double ended needle assembly 300 to expose needle 318 may be performed rearwardly of the needle to minimize the possibility of needle prick or penetration. It may be noted that in the position illustrated in FIG. 38, needle guard 316 is in its second location, as illustrated in FIG. 41.

On completion of the procedure, anterior needle 318 must be covered to prevent contact therewith by medical personnel and avoid the possibility of transmission of an infectious disease which might otherwise result. To recover the needle, needle guard 350 is gripped and translated in the direction of needle 318 to relocate needle guard 316 in its first location, as illustratd in FIGS. 35, 36 and 37. Upon rotatin of needle guard 350, hub 356 may be disengaged from boss 370. Translation of needle guard 350 posteriorly for the purpose of recovering posterior needle 352 and its enclosing sheath 354 may be effected without relocating needle guard 316 as the latter will tend to remain in its first location due to the restraining effect of ridge 308 (see FIG. 41) Upon translation of needle guard 350 from its second position back to its first position, posterior needle will be fully covered as illustrated in FIG. 39.

Referring jointly to FIGS. 42 through 50 there is illustrated a detachable single needle telescoping guard assembly 308 for attachment to a hypodermic syringe. The hypodermic syringe may be of the type illustrated and described with respect to FIGS. 28 and 29 or other type. Assembly 380 includes a body 384, a cylindrical section 406 and a guard 420 concentrically nestable with one another, as illustrated in FIG. 45. In this nested position, needle 392 is exposed to administer a medication. Body 384, supporting needle 392, includes a pair of dogs 386, 388 for threaded engagement with cylinder 186 of hypodermic syring 182 to locate hub 188 within cone shaped recess 390. A first pair of diametrically opposed channels 394, 396 extend longitudinally along body 384. Each channel includes a first location 398 at the proximal end and defined by restraining means, such as ridge 400 and a second location 402 at the distal end, which location may be defined by restraining means, like ridge 400 or a step 404, as shown.

Cylindrical section 406 includes a pair of diametrically opposed keys 408, 410 disposed at the distal end for sliding engagement with a respective one of channels 394, 396. A pair of diametrically opposed longitudinal channels are formed in the exterior surface of cylindrical section 406. Each channel includes a first location 416 at the proximal end and defined by restraining means, such as ridge 418. A second location, like those for channels 394, 396 may be included. Guard 420 includes a sleeve 422 having a pair of radially inwardly extending keys 424, 426 located at the distal end of the guard. These keys slidably engage respective ones of channels 412, 414 in cylindrical section 406. The proximal end of the guard includes a tab 428 secured at a weekend annular zone 430. Upon removal of the tab, annular weakened zone 430 will be fractured and an aperture 432 will be developed in the guard, as described previously. A cylindrical ridge 434 is incorporated in the proximal end of the guard to define an annular trough 436.

As particularly illustrated in FIGS. 47 to 50, pairs of diametrically opposed channels with corresponding keys may be employed to provide four points of support intermediate the guard, the sleeve and the body, which support is equicircumferentially located. It is also to be noted that variations of structure attendent the needle supporting body and needle guards, as described above with respect to one or another of the figures, may be incorporated in assembly 380.

In operation, single needle assembly 380 is attached to hypodermic syringe 182 by engaging dogs 386, 388 with cylinder 186, as illustrated in FIG. 43. Upon tearing away of tab 428, aperture 432 in guard 420 is developed to permit protrusion of needle 392 from within the guard, as illustrated in FIG. 44. By grasping guard 420 from a position rearwardly of needle 392 and exerting a force to translate the guard toward the hypodermic syringe, the restraining forces exerted by ridges 418 upon keys 424 and 426 (see FIG. 46) and by ridges 400 upon keys 398, cylindrical section 406 and guard 420 will become longitudinally translated toward the hypodermic syringe. During such translation, the keys will traverse their respective channels. At the point of full contraction of assembly 380, keys 398 will become lodged in second locations 402. Keys 424 and 426 will be located at the distal end of channels 412 and 414 at a second location (not identified); it is to be noted that a second location, with restraining means, such as second locations 402 may be developed in cylindrical section 406 for the purpose of engaging keys 424, 426. In the contracted state of assembly 380, as illustrated in FIG. 45, end 438 of cylindrical section 406 may bear against cylindrical ridge 434 or another part of the proximal end of guard 420. Hypodermic syringe 182 may now be used to inject a medicament.

After use of the needle and to protect the medical personnel against transmission of any infectious disease through contact with the needle or fluids dripping therefrom, guard 420 may be gripped from a location rearwardly of the needle and pushed anteriorly. The resulting movement of the guard will extend the sleeve and the guard with respect to body 384 to recover the needle and shield it against inadvertent contact. Upon such extension of the sleeve and the guard, the respective keys will be relocated in their respective first locations. Inadvertent contraction of the telescoping elements will be restrained by the respective ridges which interferingly engage with an associated key.

FIGS. 51 and 52 illustrate a variant 440 of the key associated with any of the needle guards illustrated and described previously. For manufacturing or other reasons, it may be difficult to develop a key 30 internal to a needle guard. To avoid such difficulty, variant 440 may be employed. The variant may be located at each of diametrically opposed locations of a needle guard, representatively identified by numeral 442, or only a single variant on one side of needle guard 442 may be incorporated.

Variant 400 extends longitudinally from sleeve 444 and may be formed as a part thereof. It includes an extension 446 terminated by a key 448. The extension is inwardly rotatable, as depicted by arrow 450 in FIG. 52, to locate the extension adjacent the internal surface os sleeve 444, as illustrated on the right hand side of FIG. 52. In this position, key 448 serves the identical function(s) described above with respect to key 30. Moreover, the bias force that may be provided by the bent portion 452 of extension 446 may urge key 448 radially internally to remain in engagement with any channels or restraining means associated with the key.

Depending upon numerous factors, the junction between needle guard 442 and extension 446 may be modified to facilitate the positioning of key 448 internal to the needle guard. To prevent lateral circumferential displacement of key 448 internal of sleeve 444 in response to forces imposed upon the key, a slot or groove 456 may be formed in the sleeve. This groove is configured in breadth, depth and length to relatively snugly receive extension 446, including the extended part thereof beneath key 448. The resulting mating relationship is illustrated on the right hand side of sleeve 444 in FIG. 52. It may be noted that the resilience of bent portion 452 will urge the key radially inwardly into a receiving guide channel.

For various manufacturing reasons, the pull of tabs discussed and illustrated previously, such as tab 24, may present manufacturing problems and attendant expenses of some concern. Referring jointly to FIGS. 53 and 54, there is illustrated a pop off cap 460 which may be employed as a substitute for one or another of the above described pull off tabs. As illustrated, the cap is configured to matingly, receive an anterior (needle enclosing) end of a sleeve 462 forming a part of a needle guard 464. The cap includes an outer cylindrical shroud 466 for circumferentially engaging the exterior cylindrical surface of sleeve 462. An inwardly radially displaced cylindrical shroud 468 is located to mate with the interior cylindrical surface of sleeve 462. Thereby, cap 460 nestingly receives the open end of sleeve 462. Retaining means may be employed to constrain removal of the cap and for developing a seal of sufficient quality to maintain the sleeve enclosed needle sterile. Such retaining means may include a pair of adjacent radially inwardly extending annular beads 470, 472 disposed upon the interior circumferential surface of sleeve 462. A mating annular bead 474 may extend radially outwardly from the exterior cylindrical surface of shroud 468. The relative positioning along the longitudinal axis of annular beads 470, 472 with annular bead 474 is set to provide a snap fit like engagement of annular bead 474 intermediate annular beads 470, 472. Depending upon the material, cross sectional configurations and resiliency, the mating engagement of the annular beads may be capable of providing a seal sufficient to maintain sterility of a needle enclosed within sleeve 462. To ensure sterility a length of tape may be wrapped about the sleeve and posterior end 474 of the cap.

A further variant of the pull off tabs is illustrated in FIG. 55. Herein, a sleeve 476 of a needle guard 478 includes an end 480. The end has formed as part thereof a disc like member 482. A weakened annular zone 484 extends circumferentially about member 482. To remove member 482 and permit exteriorization of the needle enclosed within sleeve 476, annular zone 484 is fractured to permit severance of the member. Such fracturing may be assisted by employment of a flange like handle 486 secured to or formed as a part of member 482 and extending therefrom. Such handle will permit manual gripping of the member by any user. Upon such gripping and exertion of a force upon handle 486 to rotate it, as depicted by double headed arrow 488, sufficient stresses can be imposed upon weakened annular zone 484 to permit fracturing of the zone and severance of member 482 from end 480.

A variant handle 490 of handle 486 is illustrated in FIG. 56. Handle 490 extends laterally in diametrically opposed directions from member 482. Such lateral extension permits the application of a substantially leveraged force upon the member to increase the ease with which the member may be rotated relative to sleeve 476 to bring about fracturing of and along weakened annular zone 484. As depicted by double headed arrow 488, handle 490 may be rotated clockwise or counterclockwise.

FIG. 57 illustrates the effect of rotating member 482. That is, rotation of the member in either direction, as depicted by arrow 488, will result in fracturing of annular zone 484. Upon such fracture, member 482 becomes severed from end 480. Upon severance, an aperture 492 is developed in end 480 through which needle 494 may be exteriorized by sliding posteriorly sleeve 476.

Body 84 for double ended needle 64, as illustrated in FIG. 13, may be difficult to manufacture in one piece or the expenses attendant such manufacture may be commercially unacceptable. Referring jointly to FIGS. 58, 59 and 60, there is illustrated a structural configuration of body 84 which may be less expensive to manufacture. It is to be understood that the structure and configuration to be described may be equally applicable to various of the double ended needle bodies described above and not just body 84. For ease of manufacture, particularly where body 84 is to be formed by man made plastic molding techniques, a mold may be developed to form the body from two halves joined together by a living hinge. More specifically, the body may be formed to have a first half 500 joined to a second half 502 by a narrow hinge 504. Body half 500 would include a trough 506 longitudinally centered therein for receiving the central part of a double ended needle 508; a similar trough 510 is longitudinally centered in and disposed along body half 502. Semi-cylindrical annular cavities 512, 514 may be disposed at one end of body 84 in axial alignment with troughs 506, 510, respectively. These cavities may be employed to retainingly receive the needle 508 and to fixedly retain the needle within body 84.

After body 84 has been formed in the configuration depicted in FIG. 58, needle 508 is inserted in one of troughs 506, 510. The two body halves are thereafter folded upon one another along hinge 504 to capture the needle within the opposing troughs and semicylindrical cavities. Alternatively, needle 508 could be staked and secured into body 84 after the body halves have been joined. To retain the body in the assembled state, a plurality of barbed prongs 520 may extend from body half 502. These prongs penetrably engage commensurately located cavities 522 in body half 500. As particularly illustrated in FIG. 59, prong 520 may include a split point 522 which must be squeezed together upon insertion into cavity 522. Barbs 524, 526 may extend laterally to mechanically engage the sidewalls of a cavity within which prong 520 is inserted. Frictional engagement between barbs 524, 526 with the corresponding walls is encouraged by the lateral forces imposed by split point 522. It is to be understood that variants of prong 520 may be developed and employed. Furthermore, prong/cavity combination may be a simply key/keyway combination to effect alignment between body halves 500, 502. In such event, retention of the body halves in the assembled state may be effected by an adhesive, mastic or an element encircling body 84; other means for securing the body halves to one another may also become apparent to those skilled in the plastics art.

As particularly depicted in FIG. 60, it is preferable that the line of demarcation 518 between body halves 500, 502 not interfere with the channels within the body and along which key 30 of an attached needle guard is translated. It may also be appreciated that with the employment of body halves, each body half may be easily formed to incorporate the channel structures for one of a pair of diametrically opposed keys of an attached needle guard.

Figure 61:
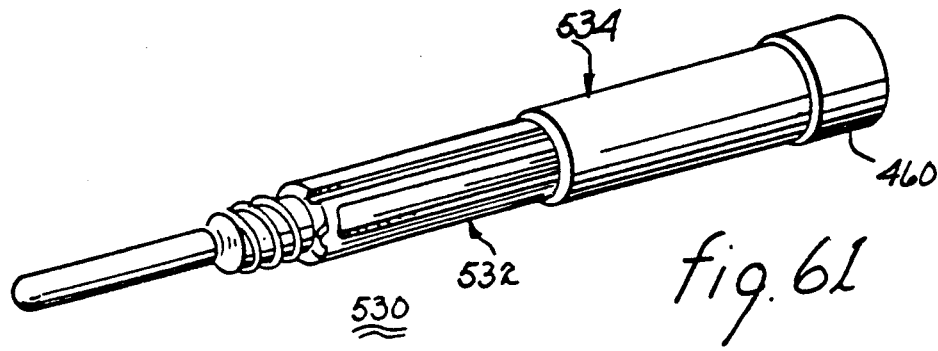
FIG. 61 illustrates a tapered double ended needle body with a matching tapered needle guard.

Under ham handed treatment, it may be possible to inadvertently disengage anteriorly a needle guard associated with one of the double ended needle bodies described above. While the interconnection between key(s) 30 extending from the needle guard with the corresponding channel in the guarded double ended needle body will prevent inadvertent disengagement anteriorly under normal operating circumstances and if due care is used, further insurance against such disengagement may be of benefit. Referring to FIG. 61, there is shown a variant 530 having a double ended needle body 532 which is tapered posteriorly from the anterior end. A similarly tapered needle guard 534 is shown mounted upon the tapered double ended needle body. This needle guard may be of the type illustrated in FIGS. 53, 54 having a cap 460 for enclosing or sealing the anterior end of the needle guard.

Figure 62:
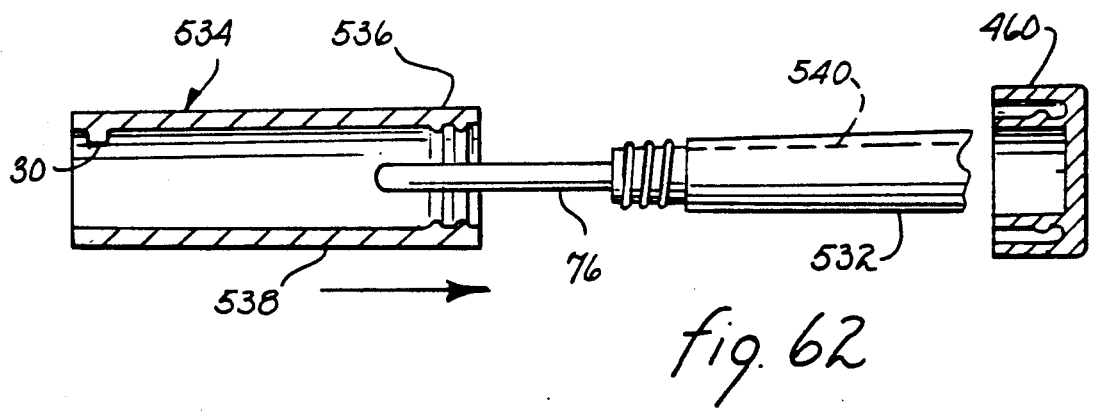
FIG. 62 illustrates a manner for mounting the needle guard upon the needle body depicted in FIG. 61.

FIG. 62 illustrates a suggested procedure for assembling double ended needle apparatus variant 530 illustrated in FIG. 61. Anterior end 536 of sleeve 538 forming needle guard 534 penetrably receives sheath 76 enclosing the posterior needle (78) extending from tapered double ended needle body 532. Upon engagement of the needle guard with the tapered double ended needle body, key 30 within sleeve 538 is brought into engagement with a guide channel 540 disposed in the body. It is to be understood that this channel may be any one of several of the configurations of channels previously illustrated. Upon positioning of needle guard 534 in its anterior most position, the anterior needle of tapered double ended needle body 532 will be encircled by end 536 of sleeve 538. Cap 460 is mated with end 536, such as in the manner described with respect to FIGS. 53 and 54. It may be noted that the attachment of cap 460 may be intended to be permanent. In such case and to exteriorize the enclosed needle, a fracturably removable member, such as member 482 illustrated in FIGS. 55, 56 and 57, may be developed upon cap 460.

Figure 63:
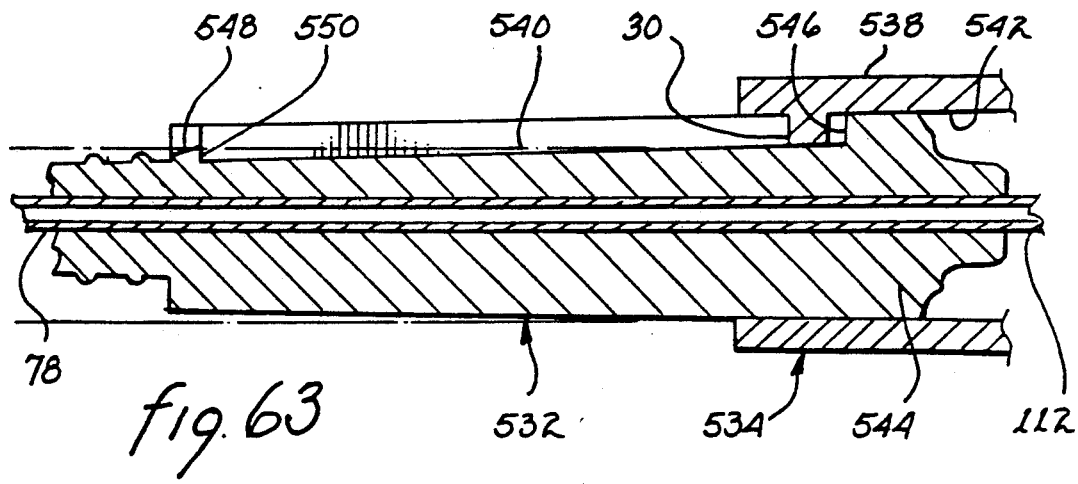
FIG. 63 is a partial cross-sectional view illustrating the interference lock between a tapered double ended needle body and a tapered needle guard.

As more particularly illustrated in FIG. 63, at the anterior most position of needle guard 534 with respect to tapered double ended needle body 532, the interior tapered cylindrical surface 542 of sleeve 538 will interferingly engage with the diametrically enlarged end 544 of tapered double ended needle body 532. Such interference will preclude further displacement of the needle guard with respect to the tapered double ended needle body except upon splitting or other mechanically destructive relief of the physical interference therebetween. The point at which interference will occur may be coincident with the travel of key 30 within channel 540 to the anterior most position. Or, as illustrated in FIG. 63, the interference may begin to be of a restraint to translational movement just prior to engagement of key 30 with end wall 546 of channel 540. In the latter event, the interference between end 544 and surface 542 will be significant and the further mechanical constraint provided by key 30 butting against end wall 546 will be a near absolute restraint against further anterior translational movement of the needle guard without breakage.

To assist in assembly of needle guard 534 upon tapered double ended needle body 530, as illustrated in FIG. 62, a ramp 548 may be employed at the posterior end of tapered double ended needle body 532, which ramp is in general alignment with channel 540. The ramp will permit key 30 to ride up over it and into channel 540 with only a slight, if any, distention of sleever 538 of the needle guard. End wall 550 formed by the ramp will limit posterior translation of the needle guard relative to the tapered double ended needle body.

In operation, an operator would receive variant 530, as illustrated in FIG. 61, except that a shield would probably enclose the posterior end of the tapered double ended needle body and the posterior needle extending therefrom. After securing the tapered double ended needle body to a container holder syringe, or the like, anterior needle 112 would be exposed by initial removal of cap 460 or a member 482 thereof. Thereafter, needle guard 534 would be translated posteriorly directly or after an initial twist or turn, depending upon the configuration of the guide channel 540 employed. Posterior translation of the needle guard would be terminated by interference between key 30 and end wall 550. After use, an operator would grasp needle guard 534 from a location posterior of needle 112 and slide the needle guard anteriorly. By appropriate matching of tapers between tapered double ended needle body 532 and tapered needle guard 524, physical interference therebetween to constrain further translational movement would occur at or about the point at which the tip of needle 112 would become encircled by the sleeve of a needle guard. Further anterior translational movement of the needle guard would frictionally lockingly locate the needle guard in it's anterior most position. Commensurate with such position, key 30 may or may not be in butting relationship with end wall 546. Further translation of the needle guard anteriorly would be precluded by the previously discussed interference fit, except upon breakage or physical damage to the components. Posterior translation of the needle guard would be restrained by the locking effect of the physical interference between the tapered double ended needle body and needle guard, with or without a positionally locked key 30, as described previously.

Various structural features and operational benefits have been described and illustrated pertinent to each of the needle guards, single needle bodies, double ended needle bodies and syringes, container holders or conduit. It is to be understood that, to the extent feasible and operationally beneficial, a feature of one element can be incorporated ab initio or as a substitute in another element even though such alternate embodiment might not have been specifically discussed and illustrated above.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirement without departing from those principles.

We claim:

1. A phlebotomy device for use with a blood collection tube, said device comprising in combination: a blood collection needle having first and second ends, means for supporting said needle and for at least partially receiving the blood collection tube in penetrable engagement with the second end of said needle, threaded means for engaging and disengaging said needle with said supporting means, a guard having an open distal end and an open proximal end, the combination of said supporting means and said needle being axially translatable along said guard to permit axial protrusion of the first end of said needle through the open distal end of said guard and outwardly of and distally from said guard for penetrating tissue and a blood vessel during a phlebotomy procedure while the second end of said needle extends proximally into fluid communication with the blood collection tube to permit infusion of a flow of blood from the blood vessel through said needle into the blood collection tube, means interengaging said guard and the combination of said supporting means and said needle for relocating said guard to expose and enclose the first end of said needle through the distal open end of said guard, said interengaging means including a reversible detent means, said reversible detent means being configured to preclude distal translation of said guard in relation to the combination of said supporting means and said needle when a first force is applied to the first end of said needle during penetration of the first end of said needle into the tissue and the blood vessel during the phlebotomy procedure and to preclude proximal translation of said guard in relation to the combination of said supporting means and said needle when a second force is applied to the second end of said needle by the blood collection tube during the phlebotomy procedure, said interengaging means further including a protrusion extending from one of said guard and the combination of said supporting means and said needle and means for engaging said protrusion, said engaging means being disposed in the other of said guard and the combination of said supporting means and said needle, said engaging means including an axially oriented single pathway during exposure and enclosure of the first end of said needle, said protrusion and said engaging means being maintained in continuous interengagement and configured to preclude independent rotation of said guard relative to the combination of said supporting means and said needle during longitudinal axial translation of the combination of said supporting means and said needle relative to said guard and to preclude disengagement of said guard relative to the combination of said supporting means and said needle upon application of any opposed radially inwardly oriented forces applied during the phlebotomy procedure to said guard distally of said protrusion and during relative translation between said engaging means and said protrusion means for restraining rectilinear disassembly of the combination of said supporting means and said needle from said guard.

2. A phlebotomy device for use with a blood collection tube, said device comprising in combination:
   a) a blood collection needle having first and second ends;
   b) means for supporting said needle and for at least partially receiving the blood collection tube in penetrable engagement with the second end of said needle;
   c) threaded means for engaging and disengaging said needle with said supporting means, said supporting means including a longitudinal axis coincident with said needle;
   d) a guard having open distal and proximal ends;
   e) means for assembling said guard onto the combination of said supporting means with said needle, said assembly means including a positive lock to prevent disassembly of said guard from the combination of said supporting means and said needle;
   f) means interengaging said guard and the combination of said supporting means and said needle for relocating said guard relative to the combination of said supporting means and said needle;
   g) detent means for positioning and maintaining said guard on the combination of said supporting means and said needle to expose the first end of said needle through the open distal end of said guard outwardly of and distally from said guard to permit penetration of tissue and a blood vessel during a phlebotomy procedure while the second end of said needle extends proximally into fluid communication with the blood collection tube to permit infusion of a flow of blood from the blood vessel through said needle and into the blood collection tube, said guard being radially repositionable with respect to the longitudinal axis of said supporting means, said detent means further including means for precluding distal translation of said guard in relation to the combination of said supporting means and said needle when a first force is applied to the first end of said needle during penetration into the tissue and the blood vessel during the phlebotomy procedure and for precluding proximal translation of said guard in relation to the combination of said supporting means and said needle when a second force is applied to the second end of said needle by the blood collection tube during the phlebotomy procedure;
   h) means for allowing a single axial pathway during exposure and enclosure of the first end of said needle; and
   i) means for restraining axial disassembly of the combination of said supporting means and said needle from said guard during rectilinear translation of the combination of said supporting means and said needle in relation to said guard.

3. A phlebotomy device for use with a blood collection tube, said device comprising in combination:
   a) a blood collection needle having first and second ends;
   b) means for supporting said needle and for at least partially receiving the blood collection tube in penetrable engagement with the second end of said needle;
   c) threaded means for engaging and disengaging said needle with said supporting means, said supporting means including a longitudinal axis coincident with said needle;

d) a guard having open distal and proximal ends;

e) a means for assembling said guard onto the combination of said supporting means with said needle, said assembly means including a positive lock to prevent disassembly of said guard from the combination of said supporting means and said needle;

f) means interengaging said guard and the combination of said supporting means and said needle for relocating said guard relative to the combination of said supporting means and said needle;

g) detent means for positioning said guard on the combination of said supporting means and said needle for exposing the first end of said needle through the distal open end of said guard outwardly of and distally from said guard to permit penetration of tissue and a blood vessel during a phlebotomy procedure while the second end of said needle extends proximally in fluid communication with the blood collection tube to permit infusion of a flow of blood from the blood vessel through said needle and into the blood collection tube, said detent means being configured to preclude rotation of said guard in relation to the longitudinal axis of said supporting means, said detent means being configured to preclude distal translation of said guard in relation to the combination of said supporting means and said needle when pressure is applied to the distal end of the first end of said needle during penetration into the tissue and the blood vessel during the phlebotomy procedure, said detent means being configured to preclude proximal translation of said guard in relation to the combination of said supporting means and said needle when pressure is applied to the proximal end of the second end of said needle with said blood collection tube during the phlebotomy procedure and said detent means being configured to preclude release of said guard from said supporting means upon application of radially inwardly oriented force applied to said detent means;

h) means for allowing a single axially oriented pathway during exposure and enclosure of the first end of said needle; and i) means for restraining axial disassembly of the combination of said supporting means and said needle from said guard during rectilinear translation of the combination of said supporting means and said needle in relation to said guard and means for precluding disengagement of said guard relative to the combination of said supporting means and said needle upon application of opposed radially oriented forces applied to said guard distally of said restraining means.

* * * * *